(12) United States Patent
Cushman et al.

(10) Patent No.: US 10,414,759 B2
(45) Date of Patent: Sep. 17, 2019

(54) PHENYLTHIAZOLES AND USES THEREOF

(71) Applicant: Purdue Research Foundation, West Lafayette, IN (US)

(72) Inventors: Mark S. Cushman, West Lafayette, IN (US); Abdelrahman S. Mayhoub, Giza (EG); Mohamed Seleem, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 15/973,569

(22) Filed: May 8, 2018

(65) Prior Publication Data

US 2018/0319784 A1 Nov. 8, 2018

Related U.S. Application Data

(60) Provisional application No. 62/502,843, filed on May 8, 2017.

(51) Int. Cl.

| C07D 417/04 | (2006.01) |
| --- | --- |
| A61K 31/506 | (2006.01) |
| C07D 417/12 | (2006.01) |
| A61P 31/04 | (2006.01) |
| A61K 31/519 | (2006.01) |
| A61K 31/5377 | (2006.01) |
| C07D 487/04 | (2006.01) |

(52) U.S. Cl.
CPC .......... *C07D 417/04* (2013.01); *A61K 31/506* (2013.01); *A61K 31/519* (2013.01); *A61K 31/5377* (2013.01); *A61P 31/04* (2018.01); *C07D 417/12* (2013.01); *C07D 487/04* (2013.01)

(58) Field of Classification Search
CPC ............................ C07D 417/04; A61K 31/506
See application file for complete search history.

(56) References Cited

U.S. PATENT DOCUMENTS

| 2004/0254192 A1* | 12/2004 | Love | C07D 277/28 514/252.05 |
| 2004/0254195 A1* | 12/2004 | Persons | C07D 211/26 514/253.11 |

OTHER PUBLICATIONS

Seleem, Second-Generation Phenylthiazole Antibiotics with Enhanced Pharmacokinetic Properties, 2017, J. Med. Chem, vol. 59, p. 4900-4912. (Year: 2017).*
CAS Reg No. 1027317-96-9, entered into STN Jun. 11, 2008. (Year: 2008).*
Dombrowski, et al., "Clinical failures of appropriately-treated methicillin-resistant *Staphylococcus aureus* infections." Journal of Infection (2008) 57, 110e115.
Chambers, "Community-Associated MRSA—Resistance and Virulence Converge." N. Engl. J. Med. 2005, 352, 1485-1487.
Moran, G., et al., "Methicillin-Resistant *S. aureus* Infections among Patients in the Emergency Department." N Engl J Med 2006;355:666-74.
Weigel, L., et al., "Genetic Analysis of a High-Level Vancomycin-Resistant Isolate of *Staphylococcus aureus.*" Science 2003, 302, 1569-1571.
French, G. L. "Bactericidal agents in the treatment of MRSA infections—the potential role of daptomycin." Journal of Antimicrobial Chemotherapy (2006) 58, 1107-1117.
Mohammad, et al., "Discovery and Characterization of Potent Thiazoles versus Methicillin- and Vancomycin-Resistant *Staphylococcus aureus.*" J. Med. Chem. 2014, 57, 1609-1615.
Mohammad, et al., Antibacterial Evaluation of Synthetic Thiazole Compounds In Vitro and In Vivo in a Methicillin-Resistant *Staphylococcus aureus* (MRSA) Skin Infection Mouse Model. pLOs oNE 2015, 10, E0142321.
Mohammad, et al., Synthesis and antibacterial evaluation of a novel series of synthetic phenylthiazole compounds against methicillin-resistant *Staphylococcus aureus* (MRSA). Eur. J. Med. Chem. 2015, 94, 306-316.

* cited by examiner

*Primary Examiner* — Karen Cheng
(74) *Attorney, Agent, or Firm* — Purdue Research Foundation; Liang Zeng Yan

(57) ABSTRACT

Series of 2-phenyl-4-methylthiazole analogs are disclosed as potential therapeutic agents for the treatment of bacterial infections, especially methicillin-resistant *Straphylococcus aureus* (MRSA) related infections. A method for the treatment of MRSA-related infections is also claimed.

15 Claims, No Drawings

PHENYLTHIAZOLES AND USES THEREOF

CROSS-REFERENCE TO RELATED APPLICATIONS

The present U.S. patent application relates to and claims the priority benefit of U.S. Provisional Patent Application Ser. No. 62/502,843, filed May 8, 2017, the content of which is hereby incorporated by reference in its entirety.

TECHNICAL FIELD

The present disclosure generally relates to a class of antibiotics, and in particular to phenylthiazole compounds as an antibiotics, especially against methicillin-resistant *Staphylococcus aureus* (MRSA).

BACKGROUND

This section introduces aspects that may help facilitate a better understanding of the disclosure. Accordingly, these statements are to be read in this light and are not to be understood as admissions about what is or is not prior art.

Infections caused by multidrug-resistant bacteria have become a global public health crisis. In particular, infections due to multidrug-resistant staphylococci have been increasing at an alarming rate. Clinically, *Staphylococcus aureus* was once susceptible to most antibiotics. However, the emergence of antibiotic-resistance in *S. aureus* has occurred in a series of waves. Starting in the mid-1940s, isolates of *S. aureus* were discovered that produced a plasmid-encoded penicillinase capable of hydrolyzing the β-lactam ring of penicillin thus rendering the antibiotic ineffective. Penicillin-resistant strains shortly began to cause community infections, and by the early 1950s they had become pandemic (P M Rountree, et al., *Med. J. Aust.* 1955, 42, 157-161). The first reports of a *S. aureus* strain that was resistant to methicillin (MRSA) were published in 1961 (M P Jevons, *Br. Med. J.* 1961, 1, 124-125). Outbreaks of infections caused by different MRSA strains were reported in hospitals in the United States in the late 1970s; by the 1980s these strains were endemic, leading to the worldwide pandemic of MRSA in hospitals that continues today. Although global in its distribution and impact, MRSA was still confined mostly to health care facilities. In 2013, the Centers for Disease Control and Prevention (CDC) reported more than 11,000 people died from a MRSA-related infection in the United States of America alone (M A Fischbach, et al., *Science* 2009, 325, 1089-1093). Egypt is among several Mediterranean countries that are experiencing a surge in MRSA infections. The prevalence of MRSA in both Egyptian community and hospital-acquired pyogenic skin and soft tissue infections is currently alarming.

Over the last 40 years, the ever-increasing burden of MRSA infections led to the increased use of vancomycin, an agent of last resort for treatment of recalcitrant MRSA infections. This intensive selective pressure resulted in the emergence of vancomycin-intermediate *S. aureus* (VISA), and vancomcyin-resistant *S. aureus* (VRSA) isolates (L M Weigel, et al, *Science* 2003, 302, 1569-1571). Compounding the problem further, the effectiveness of vancomycin is limited by prolonged, persistent or recurrent bacteremia during therapy, high rates of microbiological and clinical failures, nephrotoxicity and the increasing prevalence of non-susceptible strains (J C Dombrowski, et al, *J. Infect.* 2008, 57, 110-115).

In addition to exhibiting resistance to vancomycin, MRSA isolates resistant to a wide variety of antibacterial classes including the β-lactam antibiotics, macrolides and fluoroquinolones have been found (H F Chambers, *N. Engl. J. Med.* 2005, 352, 1485-1487; G J Moran, et al., *N. Engl. J. Med.* 2006, 355, 666-674). Collectively this points to the pressing need to develop novel antimicrobial agents.

BRIEF SUMMARY OF INVENTION

In some illustrative embodiments, this invention pertains to a compound having formula (I)

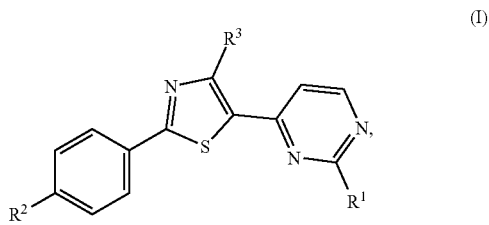

(I)

or a pharmaceutically acceptable salt, hydrate, or solvate thereof, wherein:

$R^1$ is hydrogen, an amino, alkylamino, aminoalkylamino, aminoalcohol, cycloalkylamino, hydrazines, guanidino, thioguanidino, cyano amino, acyl, ester, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, or arylalkynyl, each of which is optionally substituted; and $R^2$ is a halo, azido, cyano, nitro, hydroxy, amino, thio, carboxy, ester, amide, and derivatives thereof, and acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted; and $R^3$ is hydrogen, an alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, acyl, alkoxyl, aryl, heteroaryl, arylalkyl, arylalkenyl, or arylalkynyl, each of which is optionally substituted.

In some illustrative embodiments, this invention pertains to a compound having formula (I), wherein $R^1$ is an optionally substituted hydrazine.

In some illustrative embodiments, this invention pertains to a compound having formula (I), wherein $R^1$ is amino or an alkylamino.

In some illustrative embodiments, this invention pertains to a compound having formula (I), wherein $R^1$ is an optionally substituted guanidino.

In some illustrative embodiments, this invention pertains to a compound having formula (I), wherein $R^1$ is guanidine or 3,3-dimethylguanidino.

In some illustrative embodiments, this invention pertains to a compound having formula (I), wherein $R^2$ is n-butyl or t-butyl.

In some illustrative embodiments, this invention pertains to a compound having formula (I), wherein $R^2$ is a cycloalkyl or cycloalkenyl.

In some illustrative embodiments, this invention pertains to a compound having formula (I), wherein $R^2$ is an optionally substituted cyclohexenyl.

In some illustrative embodiments, this invention pertains to a compound having formula (I), wherein $R^2$ is an optionally substituted cyclopentenyl.

In some illustrative embodiments, this invention pertains to a compound having formula (I), wherein $R^2$ is cyclohexylidenemethyl or cyclopentylidenemethyl.

In some illustrative embodiments, this invention pertains to a compound having formula (I), wherein $R^3$ is an alkyl.

In some illustrative embodiments, this invention pertains to a compound having formula (I), wherein $R^1$ is amino, guanidine or 3,3-dimethylguanidino; $R^2$ is n-butyl; and $R^3$ is methyl.

In some illustrative embodiments, this invention pertains to a compound having formula (I), wherein $R^1$ is a hydrazine, $R^2$ is n-butyl, and $R^3$ is methyl.

In some illustrative embodiments, this invention pertains to a compound having formula (I), wherein $R^1$ is a guanidine, $R^2$ is n-butyl, and $R^3$ is methyl.

In some illustrative embodiments, this invention pertains to a compound having formula (I), wherein $R^1$ is a thioguanidine, $R^2$ is n-butyl, and $R^3$ is methyl.

In some other embodiments, this invention pertains to a pharmaceutical composition comprising a compound disclosed herein, or a pharmaceutically acceptable salt thereof, together with one or more pharmaceutically acceptable carriers, diluents, and excipients.

In some embodiments, this invention pertains to a pharmaceutical composition comprising a compound disclosed herein, in combination with one or more other therapeutically active compounds by the same or different mode of action, and one or more pharmaceutically acceptable carriers, diluents, and excipients.

In some embodiments, this invention pertains to a method for treating a patient of bacterial infection, the method comprising the step of administering a therapeutically effective amount of a compound disclosed herein, together with one or more pharmaceutically acceptable carriers, diluents, and excipients, to the patient in need of relief from said bacterial infection.

In some embodiments, this invention pertains to a method for treating a patient of bacterial infection, the method comprising the step of administering a therapeutically effective amount of a compound disclosed herein, in combination with one or more therapeutically effective compounds by the same or different mode of action, together with one or more pharmaceutically acceptable carriers, diluents, and excipients, to the patient in need of relief from said bacterial infection.

In some other embodiments, this invention pertains to a method for treating a patient of bacterial infection, the method comprising the step of administering a therapeutically effective amount of a compound of formula (I), to the patient in need of relief from said infections:

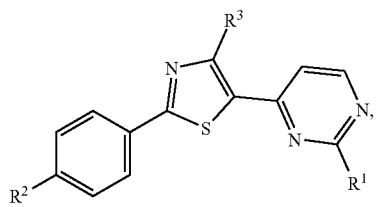

(I)

or a pharmaceutically acceptable salt, hydrate, or solvate thereof, wherein:

$R^1$ is hydrogen, an amino, alkylamino, aminoalkylamino, aminoalcohol, cycloalkylamino, hydrazines, guanidino, thioguanidino, cyano amino, acyl, ester, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, or arylalkynyl, each of which is optionally substituted;

$R^2$ is a halo, azido, cyano, nitro, hydroxy, amino, thio, carboxy, ester, amide, and derivatives thereof, and acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted; and $R^3$ is hydrogen, an alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, acyl, alkoxyl, aryl, heteroaryl, arylalkyl, arylalkenyl, or arylalkynyl, each of which is optionally substituted.

It is appreciated herein that the compounds described herein may be used alone or in combination with other compounds that may be therapeutically effective by the same or different modes of action. In addition, it is appreciated herein that the compounds described herein may be used in combination with other compounds that are administered to treat other symptoms of bacterial infections, such as compounds administered to relieve pain, nausea, vomiting, and the like.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In some illustrative embodiments, this invention pertains to a compound having formula (I)

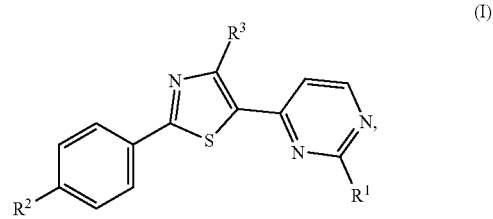

(I)

or a pharmaceutically acceptable salt, hydrate, or solvate thereof, wherein:

$R^1$ is hydrogen, an amino, alkylamino, aminoalkylamino, aminoalcohol, cycloalkylamino, hydrazines, guanidino, thioguanidino, cyano amino, acyl, ester, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, or arylalkynyl, each of which is optionally substituted; and $R^2$ is a halo, azido, cyano, nitro, hydroxy, amino, thio, carboxy, ester, amide, and derivatives thereof, and acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted; and R³ is hydrogen, an alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, acyl, alkoxyl, aryl, heteroaryl, arylalkyl, arylalkenyl, or arylalkynyl, each of which is optionally substituted.

In some illustrative embodiments, this invention pertains to a compound having formula (I), wherein R¹ is an optionally substituted hydrazine.

In some illustrative embodiments, this invention pertains to a compound having formula (I), wherein R¹ is amino or an alkylamino.

In some illustrative embodiments, this invention pertains to a compound having formula (I), wherein R¹ is an optionally substituted guanidino.

In some illustrative embodiments, this invention pertains to a compound having formula (I), wherein R¹ is guanidine or 3,3-dimethylguanidino.

In some illustrative embodiments, this invention pertains to a compound having formula (I), wherein R² is n-butyl or t-butyl.

In some illustrative embodiments, this invention pertains to a compound having formula (I), wherein R² is a cycloalkyl or cycloalkenyl.

In some illustrative embodiments, this invention pertains to a compound having formula (I), wherein R² is an optionally substituted cyclohexenyl.

In some illustrative embodiments, this invention pertains to a compound having formula (I), wherein R² is an optionally substituted cyclopentenyl.

In some illustrative embodiments, this invention pertains to a compound having formula (I), wherein R² is cyclohexylidenemethyl or cyclopentylidenemethyl.

In some illustrative embodiments, this invention pertains to a compound having formula (I), wherein R³ is an alkyl.

In some illustrative embodiments, this invention pertains to a compound having formula (I), wherein R¹ is amino, guanidine or 3,3-dimethylguanidino; R² is n-butyl; and R³ is methyl.

In some illustrative embodiments, this invention pertains to a compound having formula (I), wherein R¹ is a hydrazine, R² is n-butyl, and R³ is methyl.

In some illustrative embodiments, this invention pertains to a compound having formula (I), wherein R¹ is a guanidine, R² is n-butyl, and R³ is methyl.

In some illustrative embodiments, this invention pertains to a compound having formula (I), wherein R¹ is a thioguanidine, R² is n-butyl, and R³ is methyl.

In some other embodiments, this invention pertains to a pharmaceutical composition comprising a compound disclosed herein, or a pharmaceutically acceptable salt thereof, together with one or more pharmaceutically acceptable carriers, diluents, and excipients.

In some embodiments, this invention pertains to a pharmaceutical composition comprising a compound disclosed herein, in combination with one or more other therapeutically active compounds by the same or different mode of action, and one or more pharmaceutically acceptable carriers, diluents, and excipients.

In some embodiments, this invention pertains to a method for treating a patient of bacterial infection, the method comprising the step of administering a therapeutically effective amount of a compound disclosed herein, together with one or more pharmaceutically acceptable carriers, diluents, and excipients, to the patient in need of relief from said bacterial infection.

In some embodiments, this invention pertains to a method for treating a patient of bacterial infection, the method comprising the step of administering a therapeutically effective amount of a compound disclosed herein, in combination with one or more therapeutically effective compounds by the same or different mode of action, together with one or more pharmaceutically acceptable carriers, diluents, and excipients, to the patient in need of relief from said bacterial infection.

In some other embodiments, this invention pertains to a method for treating a patient of bacterial infection, the method comprising the step of administering a therapeutically effective amount of a compound of formula (I), to the patient in need of relief from said infections:

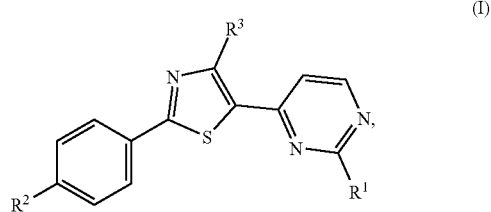

or a pharmaceutically acceptable salt, hydrate, or solvate thereof, wherein:

R¹ is hydrogen, an amino, alkylamino, aminoalkylamino, aminoalcohol, cycloalkylamino, hydrazines, guanidino, thioguanidino, cyano amino, acyl, ester, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, or arylalkynyl, each of which is optionally substituted;

R² is a halo, azido, cyano, nitro, hydroxy, amino, thio, carboxy, ester, amide, and derivatives thereof, and acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted; and R³ is hydrogen, an alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, acyl, alkoxyl, aryl, heteroaryl, arylalkyl, arylalkenyl, or arylalkynyl, each of which is optionally substituted.

It is appreciated herein that the compounds described herein may be used alone or in combination with other compounds that may be therapeutically effective by the same or different modes of action. In addition, it is appreciated herein that the compounds described herein may be used in combination with other compounds that are administered to treat other symptoms of bacterial infections, such as compounds administered to relieve pain, nausea, vomiting, and the like.

As used herein, the following terms and phrases shall have the meanings set forth below. Unless defined otherwise, all technical and scientific terms used herein have the same meaning as commonly understood to one of ordinary skill in the art.

In the present disclosure the term "about" can allow for a degree of variability in a value or range, for example, within 10%, within 5%, or within 1% of a stated value or of a stated limit of a range. In the present disclosure the term "substantially" can allow for a degree of variability in a value or range, for example, within 90%, within 95%, 99%, 99.5%, 99.9%, 99.99%, or at least about 99.999% or more of a stated value or of a stated limit of a range.

A "halogen" designates F, Cl, Br or I. A "halogen-substitution" or "halo" substitution designates replacement of one or more hydrogen atoms with F, Cl, Br or I.

As used herein, the term "alkyl" refers to a saturated monovalent chain of carbon atoms, which may be optionally branched. It is understood that in embodiments that include alkyl, illustrative variations of those embodiments include lower alkyl, such as $C_1$-$C_6$ alkyl, methyl, ethyl, propyl, 3-methylpentyl, and the like.

As used herein, the term "alkenyl" refers to an unsaturated monovalent chain of carbon atoms including at least one double bond, which may be optionally branched. It is understood that in embodiments that include alkenyl, illustrative variations of those embodiments include lower alkenyl, such as $C_2$-$C_6$, $C_2$-$C_4$ alkenyl, and the like.

As used herein, the term "alkynyl" refers to an unsaturated monovalent chain of carbon atoms including at least one triple bond, which may be optionally branched. It is understood that in embodiments that include alkynyl, illustrative variations of those embodiments include lower alkynyl, such as $C_2$-$C_6$, $C_2$-$C_4$ alkynyl, and the like.

As used herein, the term "cycloalkyl" refers to a monovalent chain of carbon atoms, a portion of which forms a ring. It is understood that in embodiments that include cycloalkyl, illustrative variations of those embodiments include lower cylcoalkyl, such as $C_3$-$C_8$ cycloalkyl, cyclopropyl, cyclohexyl, 3-ethylcyclopentyl, and the like.

As used herein, the term "cycloalkenyl" refers to an unsaturated monovalent chain of carbon atoms, a portion of which forms a ring. It is understood that in embodiments that include cycloalkenyl, illustrative variations of those embodiments include lower cycloalkenyl, such as $C_3$-$C_8$, $C_3$-$C_6$ cycloalkenyl.

As used herein, the term "alkylene" refers to a saturated bivalent chain of carbon atoms, which may be optionally branched. It is understood that in embodiments that include alkylene, illustrative variations of those embodiments include lower alkylene, such as $C_2$-$C_4$, alkylene, methylene, ethylene, propylene, 3-methylpentylene, and the like.

As used herein, the term "heterocyclic" or "heterocycle" refers to a monovalent chain of carbon and heteroatoms, wherein the heteroatoms are selected from nitrogen, oxygen, and sulfur, and a portion of which, at least one heteroatom, forms a ring. The term "heterocycle" may include both "aromatic heterocycles" and "non-aromatic heterocycles." Heterocycles include 4-7 membered monocyclic and 8-12 membered bicyclic rings, such as imidazolyl, thiazolyl, oxazolyl, oxazinyl, thiazinyl, dithianyl, dioxanyl, isoxazolyl, isothiazolyl, triazolyl, furanyl, tetrahydrofuranyl, dihydrofuranyl, pyranyl, tetrazolyl, pyrazolyl, pyrazinyl, pyridazinyl, imidazolyl, pyridinyl, pyrrolyl, dihydropyrrolyl, pyrrolidinyl, piperidinyl, piperazinyl, pyrimidinyl, morpholinyl, tetrahydrothiophenyl, thiophenyl, azetidinyl, oxetanyl, thiiranyl, oxiranyl, aziridinyl, and the like. "Heterocycles" may be optionally substituted at any one or more positions capable of bearing a hydrogen atom.

As used herein, the term "aryl" includes monocyclic and polycyclic aromatic carbocyclic groups, each of which may be optionally substituted. The term "optionally substituted aryl" refers to an aromatic mono or polycyclic ring of carbon atoms, such as phenyl, naphthyl, and the like, which may be optionally substituted with one or more independently selected substituents, such as halo, hydroxyl, amino, alkyl, or alkoxy, alkylsulfony, cyano, nitro, and the like.

The term "heteroaryl" or "aromatic heterocycle" includes substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The term "heteroaryl" may also include ring systems having one or two rings wherein at least one of the rings is heteroaromatic, e.g., the other cyclic rings can be cycloalkyl, cycloalkenyl, cycloalkynyl, aromatic carbocycle, heteroaryl, and/or heterocycle. Heteroaryl groups include, for example, pyrrole, furan, thiophene, imidazole, oxazole, thiazole, pyrazole, pyridine, pyrazine, pyridazine, and pyrimidine.

It is understood that each of alkyl, cycloalkyl, alkenyl, cycloalkenyl, alkylene, and heterocycle may be optionally substituted with independently selected groups such as alkyl, haloalkyl, hydroxyalkyl, aminoalkyl, carboxylic acid and derivatives thereof, including esters, amides, and nitrites, hydroxy, alkoxy, acyloxy, amino, alky and dialkylamino, acylamino, thio, and the like, and combinations thereof.

The term "optionally substituted," or "optional substituents," as used herein, means that the groups in question are either unsubstituted or substituted with one or more of the substituents specified. When the groups in question are substituted with more than one substituent, the substituents may be the same or different. Furthermore, when using the terms "independently," "independently are," and "independently selected from" mean that the groups in question may be the same or different. Certain of the herein defined terms may occur more than once in the structure, and upon such occurrence each term shall be defined independently of the other.

The term "patient" includes human and non-human animals such as companion animals (dogs and cats and the like) and livestock animals. Livestock animals are animals raised for food production. The patient to be treated is preferably a mammal, in particular a human being.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As used herein, the term "administering" includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically acceptable carriers, adjuvants, and vehicles.

As used herein, the term "therapeutically effective amount" refers to that amount of active compound or pharmaceutical agent that elicits the biological or medicinal response in a tissue system, animal or human that is being sought by a researcher, veterinarian, medical doctor or other clinicians, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment.

However, it is to be understood that the total daily usage of the compounds and compositions described herein may be decided by the attending physician within the scope of sound medical judgment. The specific therapeutically effective dose level for any particular patient will depend upon a variety of factors, including the disorder being treated and the severity of the disorder; activity of the specific compound employed; the specific composition employed; the age, body weight, general health, gender, and diet of the patient: the time of administration, and rate of excretion of the specific compound employed, the duration of the treatment, the drugs used in combination or coincidentally with the specific compound employed; and like factors well known to the researcher, veterinarian, medical doctor or other clinician of ordinary skill.

Depending upon the route of administration, a wide range of permissible dosages are contemplated herein, including doses falling in the range from about 1 µg/kg to about 1 g/kg. The dosage may be single or divided, and may administered according to a wide variety of dosing protocols, including q.d. (once per day), b.i.d. (twice per day), t.i.d. (three times per day), or even every other day, once a week, once a month, and the like. In each case the therapeutically effective amount described herein corresponds to the instance of administration, or alternatively to the total daily, weekly, or monthly dose, and the like.

In the search for novel antimicrobials, phenylthiazoles carrying a nitrogenous moiety at one end and lipophilic part at the opposite side were previously reported as a new antimicrobial scaffold with potent activity against multi-drug-resistant strains of S. aureus, including MRSA and VRSA (Mohammad, H, et al., J. Med. Chem. 2014, 57, 1609-1615). These phenylthiazole antibacterials possess a selective advantage over vancomycin in their ability to rapidly eradicate a high inoculum of MRSA. This is clinically significant for the treatment of diseases caused by staphylococci, as it will impact the size and timing of doses administered to MRSA-infected patients (G L French, J. Antimicrob. Chemother. 2006, 58, 1107-1117). The highly promising in vivo antimicrobial activity of the discovered phenylthiazole class of antibacterials, either as a single agent or in combination with other therapeutic agents, as thus far been hampered by their poor pharmacokinetic profile (H Mohammad, et al., PloS One 2015, 10, e0142321). For instance, the lead compound 1 is rapidly cleared by human liver microsomes resulting in a relatively short half-life (<30 minutes). Designing compounds with a longer duration is important to ensure the active compound stays in circulation long enough to reach the target site of infection and exert its antibacterial effect.

In this investigation, a strategy was proposed to overcome the metabolic instability of the aminoguanidine moiety utilizing ligand-based drug design approaches given that the exact molecular target of these phenylthiazoles has not been identified yet. To date, all first generation phenylthiazoles carry a hydrolyzable C=N linkage, which contributes to their metabolic instability and short $t_{1/2}$. All attempts to replace the hydrolyzable C=N with more metabolically stable C—N or amide bonds resulted in less active compounds (H Mohammad, et al., Eur. J. Med. Chem. 2015, 94, 306-316). These results, collectively, pointed to the importance of "linker conformational-restriction". Therefore, in this study we propose that incorporating the hydrolysable Schiff base moiety within an aromatic ring system will enhance the overall metabolic stability of the phenylthiazoles while keeping the required conformational-restriction. Thus, several phenylthiazoles bearing, at thiazole position-5, a pyrimidine ring connected with guanidine, or guanidine-like moiety have been proposed.

Chemistry. Thioamide 2 was treated with α-chloroacetylacetone to yield phenylthiazole derivative 3 (Scheme 1). The later compound was allowed to react with dimethylformamide-dimethylacetal (DMF-DMA) to give the first key intermediate 4. Finally, the methylsulfonyl derivative 7 was easily obtained by allowing enaminone 4 to react with thiourea followed by methylation and oxidation of the free thiol group as detailed in Scheme 1.

The enaminone moiety of compound 4 revealed two distinct doublet signals in the $^1$H NMR spectrum at 7.69 and 5.44, each of one proton, with coupling constant of 12 Hz, characteristic to the E-configuration. Upon cyclization of compound 5, the chemical shifts of those two signals were shifted to a higher field and their J value decreased to be around 5 Hz. The inserted S-methyl group of compound 6 was represented in $^1$H NMR spectrum by one extra singlet signal in the aliphatic region at δ 2.55. This signal was shifted downfield to 2.93 ppm upon oxidation of S-mercaptyl group into the methylsulfonyl analogue 7.

Scheme 1. Synthesis of key intermediates 4 and 7*

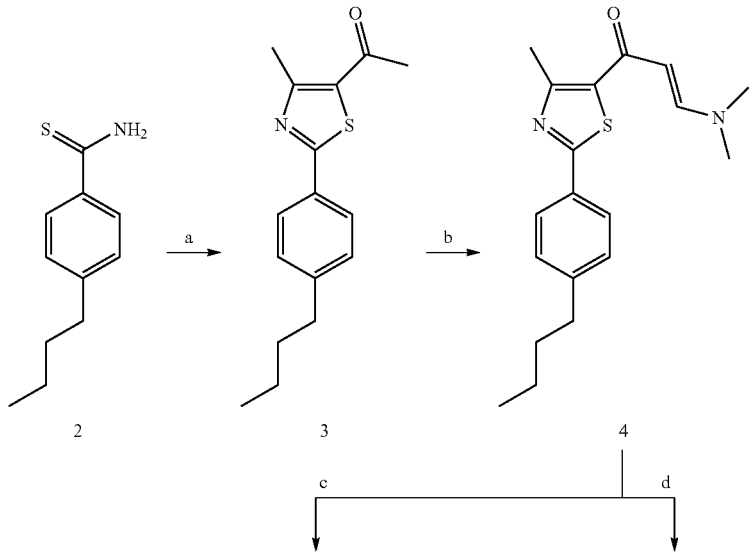

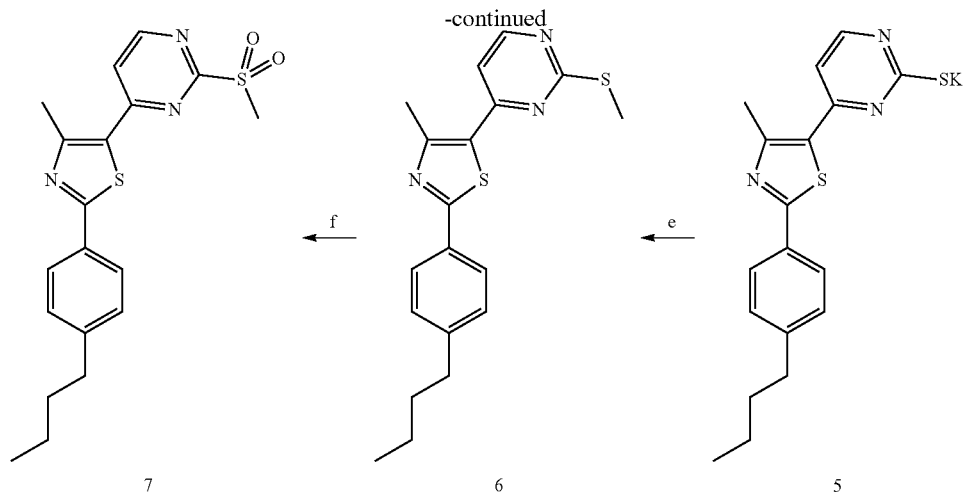

*Reagents and conditions: (a) absolute EtOH, 3-chloropentane-2,4-dione, heat to reflux, 12 h; (b) DMF—DMA heat at 80° C., 8 h; (c) S-methylisothiourea hemisulfate, K$_2$CO$_3$, EtOH, heat to reflux, 6 h; (d) thiourea, KOH, EtOH, heat to reflux, 8 h; (e) dimethyl sulfate, KOH, H$_2$O, stirring at 23° C., 12 h; (f) MCPBA, dry DCM, stirring at 23° C., 16 h.

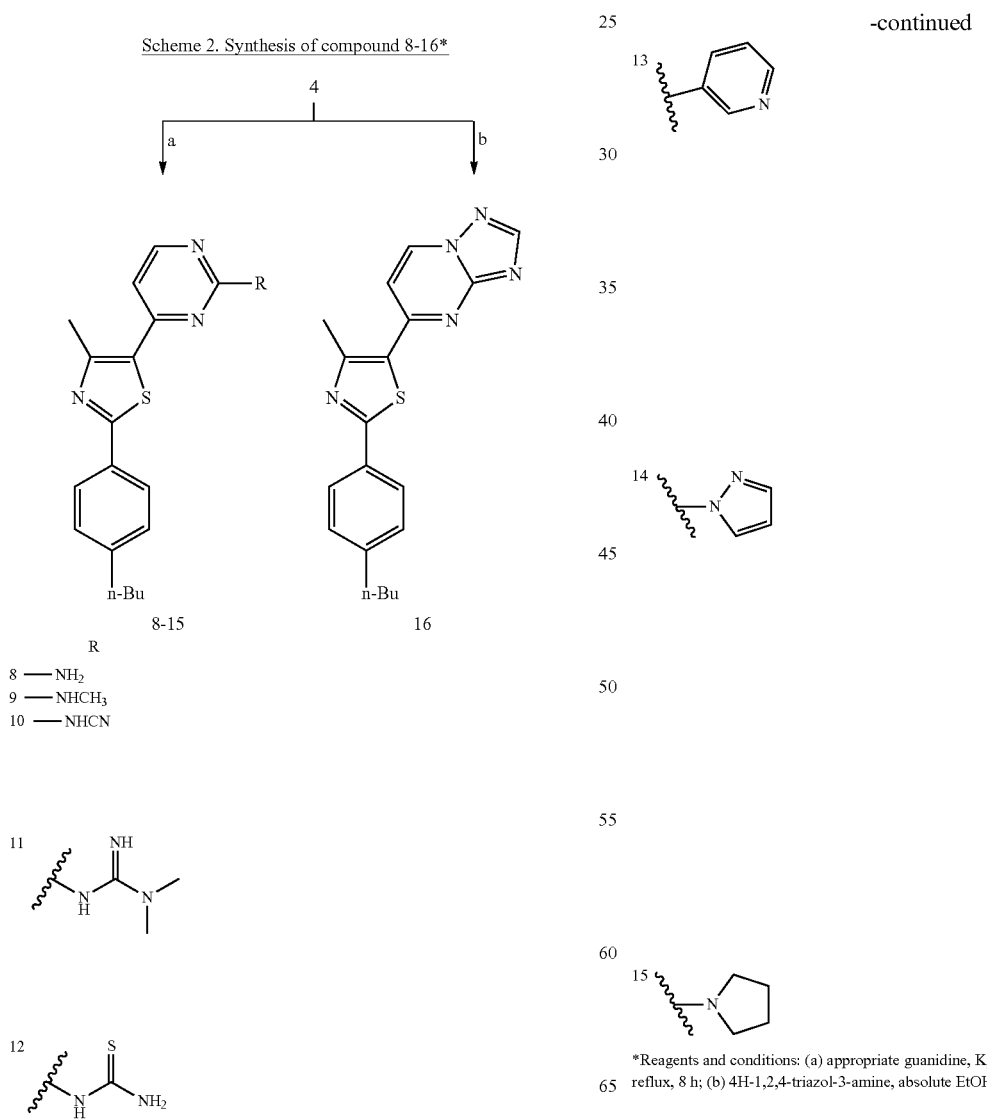

*Reagents and conditions: (a) appropriate guanidine, K$_2$CO$_3$, absolute EtOH, heat to reflux, 8 h; (b) 4H-1,2,4-triazol-3-amine, absolute EtOH, heat to reflux for 5 h.

Scheme 3. Synthesis of compounds 17-19*
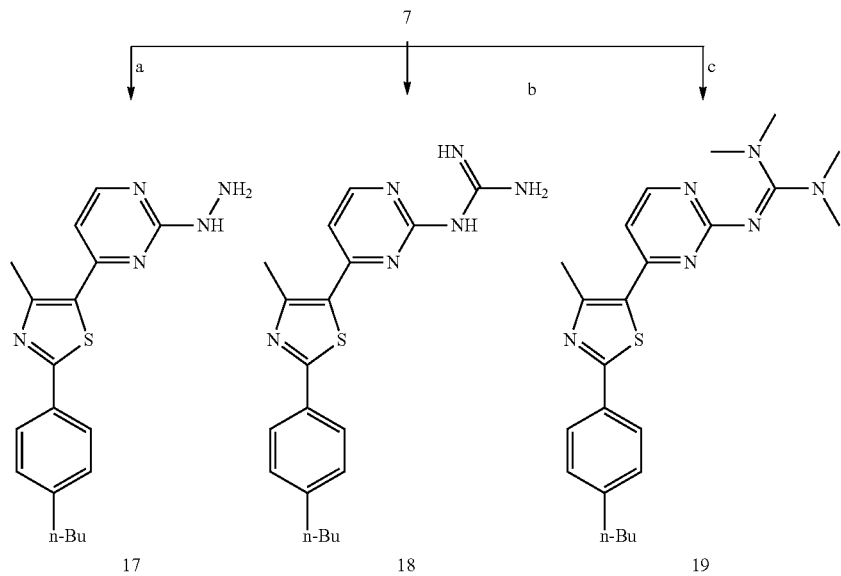
*Reagents and conditions: (a) NH₂NH₂·H₂O, DMF, heat at 80° C. for 0.5 h; (b) guanidine HCl, DMF, heat at 80° C. for 2 h; (c) tetramethylguanidine, DMF, heat at 80° C. for 2 h.
Scheme 4. Synthesis of 24-35*
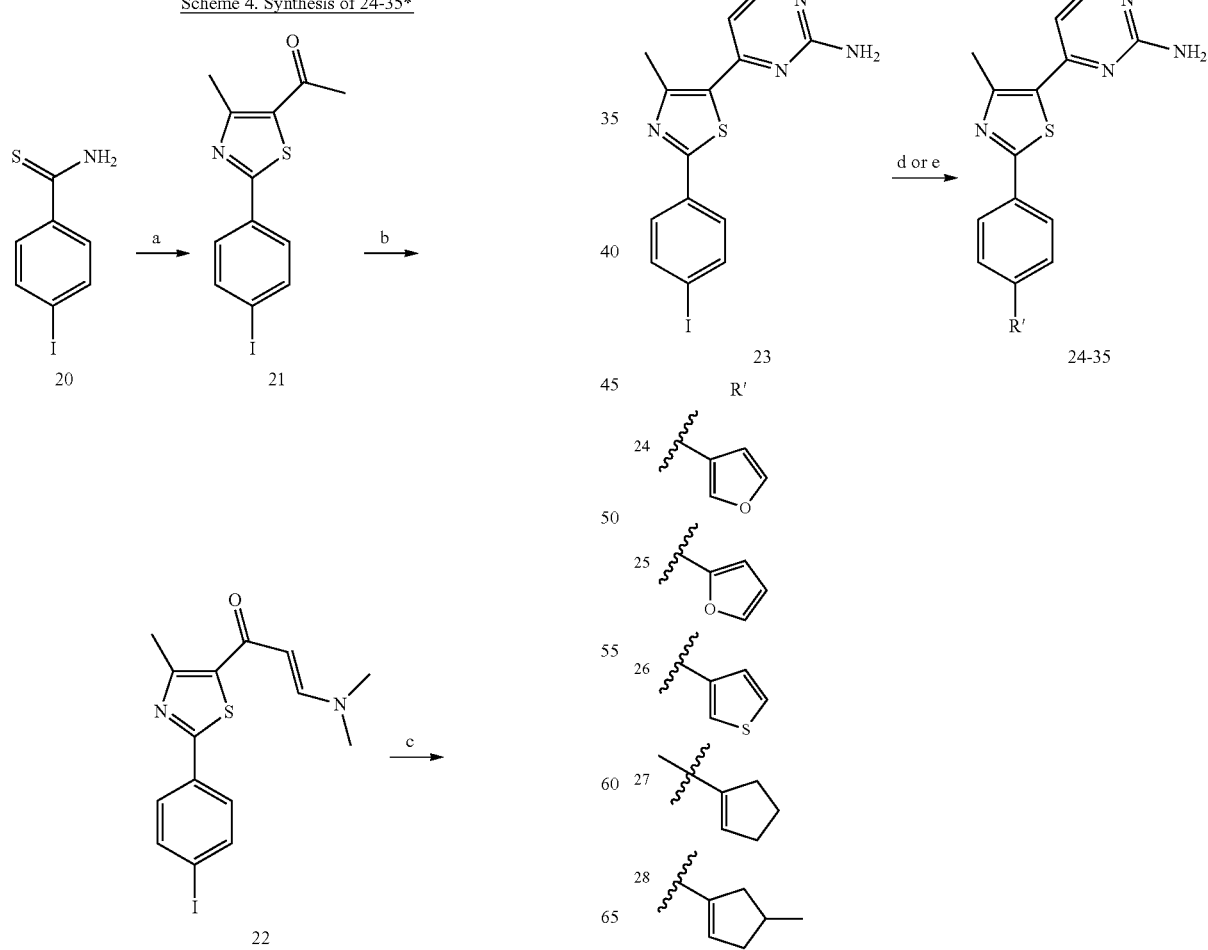

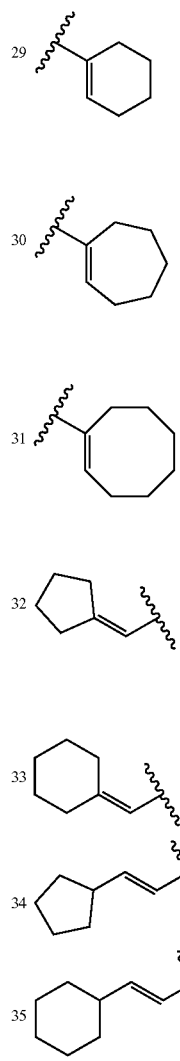

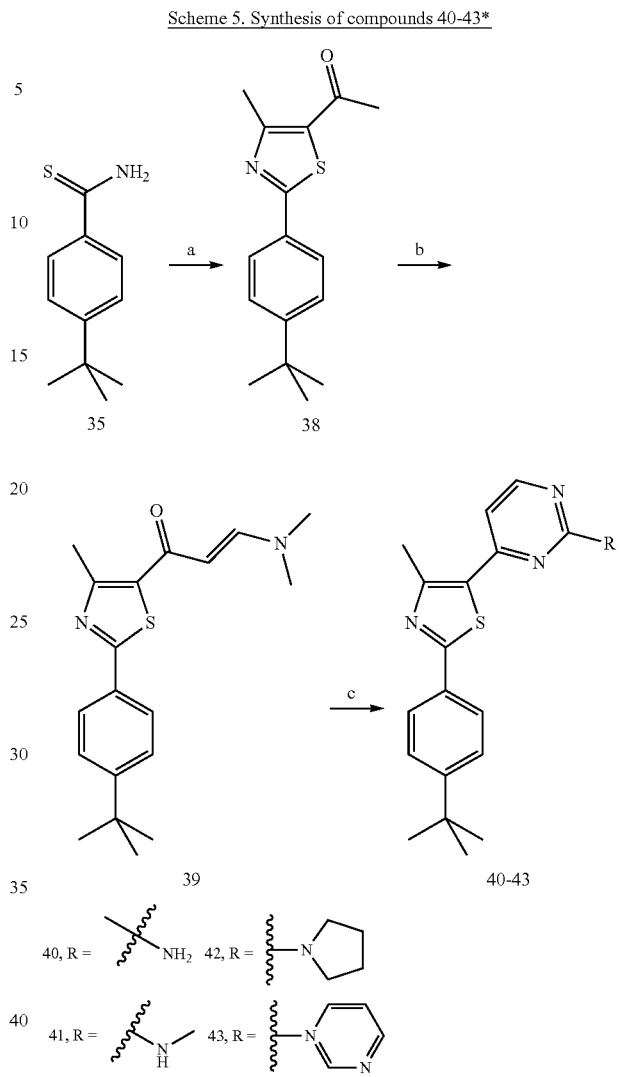

Scheme 5. Synthesis of compounds 40-43*

*Reagents and conditions: (a) Absolute EtOH, 3-chloropentane-2,4-dione, heat at reflux, 12 h; (b) DMF—DMA heat at 80° C., 8 h; (c) proper imidamidate, K₂CO₃, absolute EtOH, heat at reflux, 3-8 h.

*Reagents and conditions: (a) Absolute EtOH, 3-chloropentane-2,4-dione, heat to reflux, 12 h; (b) DMF—DMA 100° C., 8 h; (c) guanidine hydrochloride, K₂CO₃, EtOH, heat to reflux, 12 h; (d) boronic acid derivative, XPhos Pd G2, dry DMF, K₂CO₃, 85° C., MW, 1 h; (e) proper alkene, dry DMF, Pd(OAc)₂, Et₃N, 80° C., 2 h.

With enaminone key intermediate 4 in hand, nine 5-pyrimidinylphenylthiazoles were obtained via reaction with different nucleophiles (Scheme 2). Finally, methylsulfonyl intermediate 7 was utilized to complete this series of optimized phenylthiazoles at position-5. Hence, the methylsulfonyl moiety was replaced by three nucleophiles; namely: hydrazine hydrate, guanidine hydrochloride and tetramethylguanidine, to afford the final products 17-19, respectively (Scheme 3).

The para-iodo intermediates 21 and 22 necessary for the subsequent chemical transformations (compounds 23-35) have been synthesized in a similar manner as the corresponding n-butyl analogues 4 and 7 as detailed in Scheme 4.

So far, three aromatic analogues to n-butyl moiety have been obtained via Suzuki cross coupling using the 2n$^d$ generation pre-made Xphos Pd catalyst (Scheme 4). The $^1$H NMR spectra of compounds 24-26 showed three extra signals each, in the aromatic region, corresponding to the furyl and/or thienyl moieties (see Experimental part).

On the other hand, a series of cycloalkenes have been tethered to the phenyl group para-position via Heck cross coupling using a standard protocol; i.e. palladium acetate and triethylamine in a dry DMF (Scheme 4). Similarly, four terminal alkenes have been allowed to react with the 4-iodophenylthiazole 23 using the same protocol (Scheme 4).

Phenylthiazole 38 was prepared from 4-t-butylthiobenzamide as reported previously (L M Weigel, et al., Science 2003, 302, 1569-1571). Treatment of 38 with DMF-DMA under solvent-free conditions afforded enaminone 39 in almost quantitative yield, which was allowed to react with different carboximidamides to provide the final products 40-43 (Scheme 5).

Next, the 2-(methylsulfonyl) pyrimidine 46 was obtained from the corresponding enaminone 39 via three consecutive steps; reaction with thiourea followed by methylation and oxidation with mCPBA (Scheme 6). Nucleophilic substitution on the methylsulfonyl moiety with different nitrogenous nucleophiles afforded the final products 47-64 (Scheme 6).

Scheme 6. Synthesis of compounds 47-64*

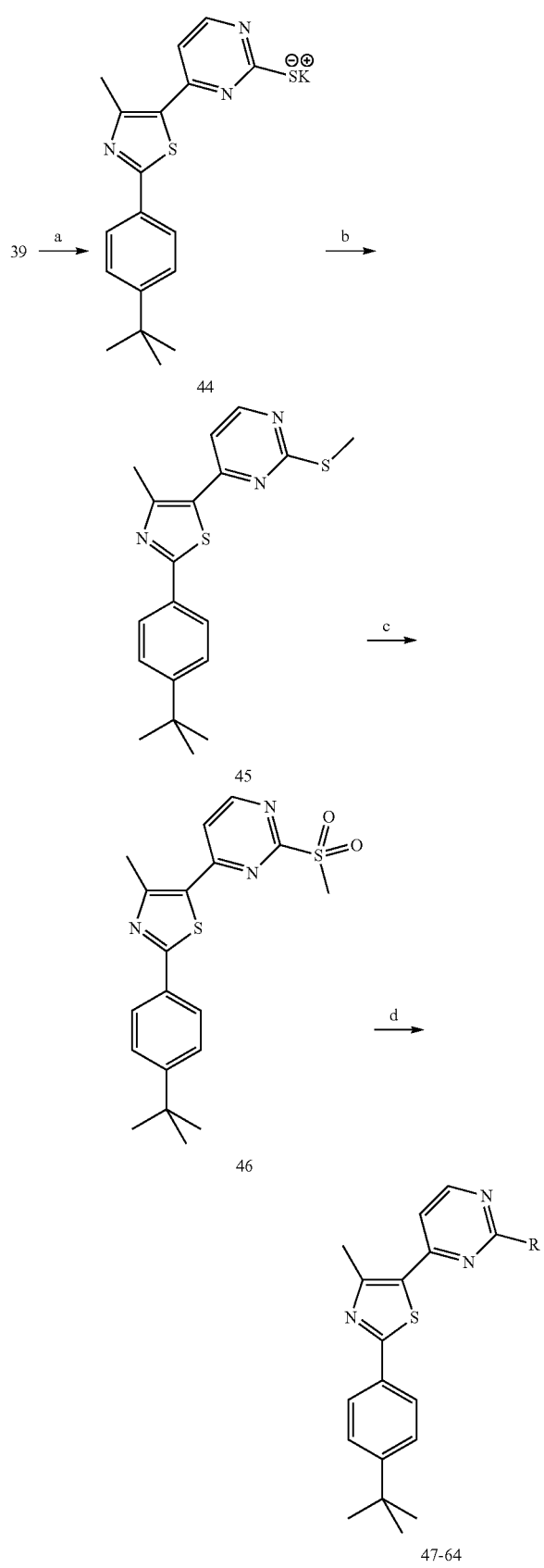

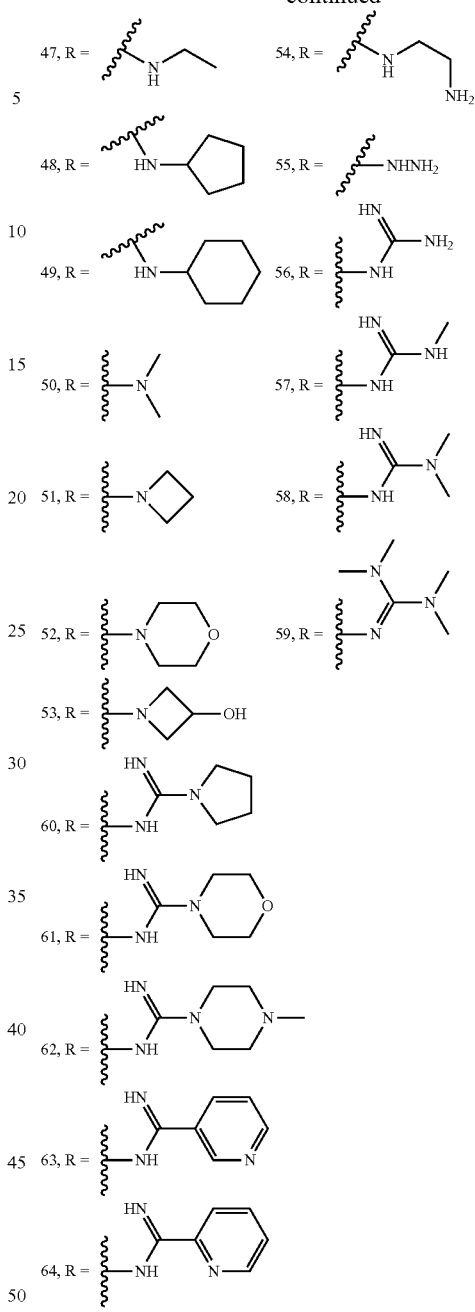

* Reagents and conditions: (a) thiourea, KOH, EtOH, heat at reflux, 8 h; (b) dimethyl sulfate, KOH, H$_2$O, stirring at 23° C., 2 h; (c) MCPBA, dry DCM, stirring at 23° C., 16 h; (d) appropriate amine, hydrazine, guanidine or carboximidate, dry DMF, heat at 80° C. for 0.5-8 h Biological Results.

A. Anti-MRSA Activity.

At the outset of our study, the hypothesis of replacing the hydrolyzable Schiff base moiety with a pyrimidine ring was first tested by synthesizing the simplest 2$^{nd}$ generation derivative with an aminopyrimidine group at the thiazole position-5. So far, the aminopyrimidine derivative 8 inhibited MRSA at a value (3.12±0.10 μg/mL) slightly better than the 1$^{st}$ generation lead compound 1 that had a minimum inhibitory concentration (MIC) value of 4.8 μg/mL against the same MRSA strain (Table 1). Fortunately, the intrinsic $t_{1/2}$ of the first derivative in the $2^{nd}$ generation was seven times (195 min, Table 2) higher than the lead compound 1 (28.8 min, Table 2).

With this solid evidence in hand, the free amino group was replaced with different nitrogenous moieties in order to address the structure-activity-relationships (SARs) around what is identified previously as "the cationic part". Adding a methyl group to the terminal nitrogen (compound 9) or nitrile group (compound 10) dramatically decreased the antibacterial activity, mostly due to the poor solubility issues under the testing conditions.

Next, the guanidine-like moiety of 8 was replaced with a true guanidinyl group and compound 18 was prepared. The antibacterial activity of 18 was on par with vancomycin, the drug of choice for treatment of systemic MRSA infections; hence both compounds possessed a MIC value of 1.56 μg/mL (Table 1). This value is three times better than that of the lead compound 1 and two-fold better than the first lead in $2^{nd}$ generation (compound 8). Altering the lipophilic properties of compound 18 by replacement of the NH with a sulfur atom (compound 12) led to complete abolishment of the anti-MRSA activity (Table 1). On the other hand, decreasing the polarity of the guanidinyl moiety by adding two methyl groups (compound 11) provided the first derivative in this series with MIC value below one microgram/mL. This observation sheds lights on a possible favorable lipophilic region around the terminal nitrogen. This hypothesis was explored with the simplest derivative in this set of compounds (compound 8) by incorporating the free amine within a pyrrolidine ring (compound 15). Unfortunately, the pyrrolidinyl derivative 15 lacks any antibacterial activity. This second observation provided insight into the importance of having a "hydrogen-bond donor" within the cationic part. Moving back to the 2-guanidinylpyrimidine scaffold, the tetramethylguanidine derivative 19 was synthesized to test the later hypothesis. Unlike the guanidine derivative 18, the corresponding tetramethyl analogue 19 revealed no antibacterial efficacy (Table 1). This observation confirms our second hypothesis of the importance of having a "HBD" within the nitrogenous side chain is necessary for anti-MRSA activity.

Based on the learning from the previous results, a second "HBD" was added to the amino group of compound 8 and the hydrazino analogue 17 was prepared, which inhibited the growth of MRSA at 0.4 μg/mL (Table 1). The hydrazino derivative 17 demonstrated a 12-fold improvement in its MIC value when compared with the lead compound 1 and was eight times more active than the first derivative in the $2^{nd}$ generation phenylthiazoles antibiotics (compound 8). The antibacterial activity of 17 was further evaluated against a panel of MSSA, MSRA and VRSA clinical isolates (Table 3), and it was comparable with vancomycin and linezolid. In addition, compound 17 showed drastic superiority with vancomycin-resistant strains (VRSA10 & VRE ATCC 700221). Subsequent aromatization of the hydrazino moiety provided pyrrazolylpyrimindine analogue 14 or its pyridinylpyrimidine derivative 13 that exhibited no antibacterial activity. This observation further confirms our previous assumption that the "nitrogenous side chain has to include, at least, one HBD".

TABLE 1

Antimicrobial activity (μg/mL) of $2^{nd}$ generation phenylthiazoles vs. MRSA (2658 RCMB).

| Entry | R | Cpd | MIC ± SD (μg/mL) | Entry | R' | Cpd | MIC ± SD (μg/mL) |
|---|---|---|---|---|---|---|---|
| 1 | NA | 1 | 4.8 ± 0.0 | 16 | I | 23 | >25 |
| 2 | NA | 4 | >25 | 17 | 3-furyl | 24 | 7.8 ± 0.5 |
| 3 | —NH₂ | 8 | 3.12 ± 0.10 | 18 | 2-furyl | 25 | 8.7 ± 0.3 |
| 4 | —NHCH₃ | 9 | >25 | 19 | 3-thienyl | 26 | 6.25 ± 0.0 |

TABLE 1-continued
Antimicrobial activity (μg/mL) of 2$^{nd}$ generation phenylthiazoles vs. MRSA (2658 RCMB).
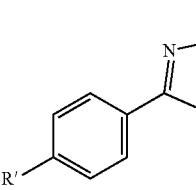
| Entry | R | Cpd | MIC ± SD (μg/mL) | Entry | R' | Cpd | MIC ± SD (μg/mL) |
|---|---|---|---|---|---|---|---|
| 5 | —NHCN | 10 | 18.7 ± 2.3 | 20 | 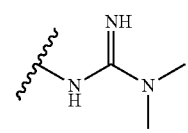 [SMILES: *NC(=N)N(C)C] | 27 | 3.12 ± 0.00 |
| 6 | 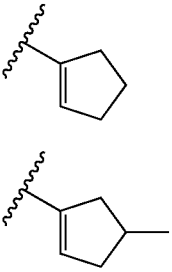 | 11 | 0.78 ± 0.00 | 21 | 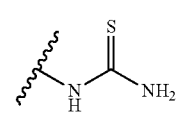 | 28 | 3.8 ± 0.4 |
| 7 | 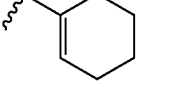 | 12 | >25 | 22 | 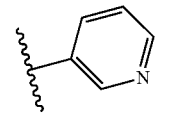 [SMILES: *c1cccnc1] | 29 | 0.78 ± 0.00 |
| 8 | 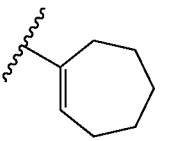 | 13 | 17.2 ± 0.4 | 23 | 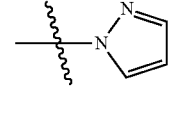 [SMILES: *n1cccn1] | 30 | 3.12 ± 0.00 |
| 9 | 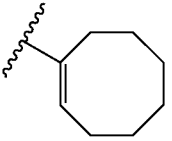 [SMILES: */C1=C/CCCCCC1] | 14 | >25 | 24 | 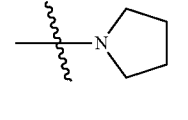 | 31 | 5.60 ± 0.10 |
| 10 | 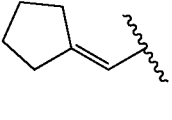 [SMILES: *C=C1CCCC1] | 15 | >25 | 25 | 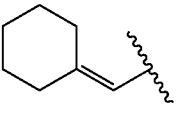 [SMILES: *C=C1CCCCC1] | 32 | 1.17 ± 0.19 |
| 11 | NA | 16 | >25 | 26 | 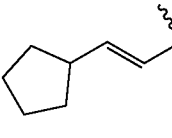 | 33 | 1.56 ± 0.00 |
| 12 | —NH—NH$_2$ | 17 | 0.40 ± 0.0 | 27 | 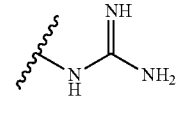 | 34 | 3.12 ± 0.00 |
| 13 | 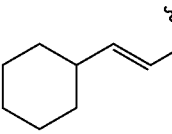 | 18 | 1.56 ± 0.10 | 28 | | 35 | 3.12 ± 0.00 |

TABLE 1-continued

Antimicrobial activity (μg/mL) of $2^{nd}$ generation phenylthiazoles vs. MRSA (2658 RCMB).

| Entry | R | Cpd | MIC ± SD (μg/mL) | Entry | R' | Cpd | MIC ± SD (μg/mL) |
|---|---|---|---|---|---|---|---|
| 14 | (N,N',N'-trimethylguanidinyl) | 19 | >25 | 29 | vancomycin | | 1.56 ± 0.00 |

TABLE 2

Evaluation of metabolic stability of tested compounds, verapamil, and warfarin, in human liver microsomes.

| Tested compound | NADPH-dependent $CL_{int}$ (μL/min-mg) | NADPH-dependent $t_{1/2}$ (min) | NADPH-free $Cl_{int}$ (μL/min-mg) | NADPH-free $t_{1/2}$ (min) |
|---|---|---|---|---|
| 1 | 80.3 | 28.8 | 0.5 | >60 |
| 8 | 3.3 | 195 | 0.5 | >60 |
| 11 | 7.5 | 243 | 0.5 | >60 |
| 17 | 3 | 308 | 0.5 | >60 |
| Verapamil | 201 | 11 | 1 | >60 |
| Warfarin | 0.3 | >60 | 0.0 | >60 |

$CL_{int}$ = microsomal intrinsic clearance;
$t_{1/2}$ = half-life

TABLE 3

Minimum inhibitory concentration (MIC in μg/mL) and Minimum bactericidal concentration (MBC μg/mL) of compound 17, vancomycin and linezolid screened against a panel of S. aureus and vancomycin-resistant Enterococcus faecium (VRE) clinical isolate strains.

| | | 17 | Vancomycin | Linezolid |
|---|---|---|---|---|
| NRS72 (MSSA) | MIC | 2 | 2 | 1 |
| | MBC | 8 | 2 | 2 |
| NRS119 (MRSA) | MIC | 2 | 1 | 32 |
| | MBC | 2 | 1 | >64 |
| NRS123 (MRSA USA400) | MIC | 2 | 1 | 1 |
| | MBC | 2 | 1 | 16 |
| NRS382 (MRSA USA100) | MIC | 2 | 1 | 1 |
| | MBC | 4 | 1 | 8 |
| NRS383 (MRSA USA200) | MIC | 2 | 1 | 1 |
| | MBC | 2 | 1 | 32 |
| NRS384 (MRSA USA300) | MIC | 2 | 1 | 1 |
| | MBC | 2 | 1 | 4 |
| VRSA10 | MIC | 1 | >64 | 1 |
| | MBC | 2 | >64 | 2 |
| VRE ATCC 700221 | MIC | 2 | >64 | 1 |
| | MBC | 8 | >64 | 32 |

TABLE 4

Evaluation of solubility of tested compounds, reserpine, tamoxifen, and verapamil in phosphate buffered saline (PBS).

| Compound Tested | Solubility limit* (μM) |
|---|---|
| Lead compound (1) | 62.5 |
| 8 | 42 |
| 11 | 53 |
| 17 | 55 |
| 24 | 13 |
| 25 | 14 |
| 26 | 8.5 |
| 27 | 35 |
| 29 | 37 |
| Reserpine | 31.3 |
| Tamoxifen | 15.6 |
| Verapamil | >500 |

*Solubility limit corresponds to the highest concentration of test compound where no precipitate was detected (OD540).

B. Cytotoxicity.

The cytotoxicity impact of the $2^{nd}$ generation compounds, represented by the most potent derivative 17, was analyzed against human keratinocytes (HaCaT) and compared with the $1^{st}$ generation compounds, represented by the lead compound 1. Compound 1 was nontoxic up to a concentration of 16 μg/mL. The toxicity profile of the $2^{nd}$ generation derivative 17 showed significant improvement as it was not toxic up a concentration of 64 μg/mL, which is 160 times more than the MIC value found against MRSA.

C. Physiochemical Properties and Pharmacokinetic Profiling.

Thus far, the newly developed $2^{nd}$ generation derivatives displayed improved antibacterial activity and an enhanced safety profile in relation to the $1^{st}$ generation compounds. We next moved to examine the "drug-like" properties of the most promising candidate to determine its suitability for further investigation. Drug discovery is a complex process that includes multiple lines of investigation, often with conflicting goals, that necessitates data integration in order to achieve a balanced clinical candidate. Those candidates must possess a good PK profiles and physiochemical properties. In this regard, the solubility and apparent permeability of some selected members of the $2^{nd}$ generation series of compounds were examined in comparison with the lead compound 1 and reference drug molecules. Table 4 demonstrated that tethering the cationic part of the phenylthiazole moiety via a pyrimidine ring resulted in a considerable decrease in aqueous solubility. The aminopyrimidine derivative 8 was found to be 32% less soluble than the lead compound 1 (Table 4). Expanding the polar surface area of the cationic part via replacement of the free amino group of 8 with a hydrazide or guanidine moiety had a positive impact on improving the compound's aqueous solubility as measured by the turbidometric solubility assay. Hence, the aqueous solubility increased from 42 µM, in the case of compound 8, into 53 and 55 µM, in the case of compounds 11 and 17, respectively (Table 4); however, both values are still below that of lead compound 1 but better than the two tested FDA-approved drugs tamoxifen and reserpine (Table 4).

Aqueous solubility is not the only factor that determines oral bioavailability; permeability has also a great impact. In the present work, the Caco-2 bidirectional permeability assay was used to examine the permeability profile of the lead compound in this series (compound 8), with that of the $1^{st}$ generation lead structure 1. The values obtained were compared with two control drugs, one with limited permeability properties (ranitidine) and one with a strong permeability profile (warfarine). Although compound 8 did not possess as strong a permeability profile as warfarin, it exhibited a notable improvement relative to the previously reported poor permeability properties of the lead compound 1 (Table 5). The Caco-2 apparent permeability, $P_{app}$ (A→B) was significantly improved from 0.0, in the case of 1, to $14.9 \times 10^{-6}$ cm/s with compound 8. In the same vein, the $P_{app}$ (B→A) value also improved by a factor of 14. These results collectively point out the superiority of the $2^{nd}$ generation phenylthizoles over the older $1^{st}$ generation analogues.

TABLE 5

Evaluation of apparent permeability of tested compound, ranitidine, and warfarin, via the Caco-2 permeability assay.

| Compound Tested | Mean A→B$^a$app ($\times 10^{-6}$ cm/s) | Mean B→A$^b$app ($\times 10^{-6}$ cm/s) | Efflux ratio$^c$ |
|---|---|---|---|
| Lead compound (1)[23] | 0.0$^d$ | 1.2 | >2 |
| 8 | 14.9 | 17.0 | 1.1 |
| 17 | 1.6 | 2.8 | 1.8 |
| Ranitidine | 0.2 | 1.7 | 8.5 |
| Warfarin | 27.6 | 11.1 | 0.4 |

$^a$Mean A→B $P_{app}$ = mean apparent permeability of test compound from apical to basolateral surface.
$^b$Mean B→A $P_{app}$ = mean apparent permeability of test compound from basolateral to apical surface.
$^c$Efflux ratio = $P_{app}$ (B→A)/$P_{app}$ (A→B)
$^d$Compound not detected in receiver compartment (peak below limit of detection); permeability may be underestimated.

It has already been reported that the lead compound 1 was cleared by liver microsomes at a rate of 80.3 µL/min-mg and had a half-life just below half an hour.[23] In this study, the three tested compounds 8, 11 and 17, one from each subclass, were found to possess metabolic clearance rates ranging between 3 and 7.5 µL/min-mg (Table 2). These values denote that $2^{nd}$ generation phenylthiazoles exhibit 10 to 27-fold improvements in how rapidly they are metabolized and cleared from liver cells compared to the $1^{st}$ generation.

Encouraged by the promising in vitro results, the pharmacokinetic parameters of the most promising candidate thus far, compound 17, were determined using SD rats. Thence, three animals were dosed with compound 17 (50 mg/Kg) orally and plasma samples were collected over a 24 h period. The PK curve preliminarily suggests a once daily dose. Interestingly, compound 17 was detected in plasma in the microgram range ($C_{max}$=9.3 µg/mL), well above the MIC value, which reflects the good permeability and absorption properties determined from the Caco-2 permeability and turbidometric solubility analysis described above. The in vivo mean residence time (MRT) for 17 was approximately 8 h (Table 6). Finally, these data collectively provide solid evidence that this new generation of phenylthiazoles, unlike previously reported derivatives, is no longer P-gp substrates and is metabolically stable.

TABLE 6

Compound 17 plasma pharmacokinetic parameters following single oral dose (30 mg/Kg) to rats

| $C_{max}$ (ng/mL) | $t_{max}$ (h) | $AUC_{last}$ ((h) * (ng/mL)) | $\lambda z$ (1/h) | $AUC_{tot}$ ((h) * (ng/mL)) | $t_{half}$ (h) | MRT (h)$^a$ |
|---|---|---|---|---|---|---|
| 9326.32 | 4.67 | 83173.60 | 0.19 | 100010.96 | 8.24 | 7.74 |

$^a$Mean residence time

The main drawback of several commercial antimicrobials used to treat MRSA infections is that they are bacteriostatic (such as linezolid); i.e. they have the ability of inhibiting bacterial growth but they do not kill the bacteria, or they exhibit a very slow bactericidal mode of action (such as vancomycin) resulting in difficulty in clearing an infection.[29,30] An antibacterial agent that demonstrates the ability to rapidly eradicate MRSA would reduce the likelihood of rapid bacterial resistance emerging to this agent. To examine the antibacterial activity of the most promising analogues constructed thus far, a time-kill assay was performed using the most active compound 17 tested against MRSA US300 strain. This strain is responsible for most cases of community-acquired MRSA (CA-MRSA) infections, MRSA skin and soft tissue infections (SSTIs) in the United States of America and other countries around the world, and pneumonia as well. The lead compound 1 required 6 h to logarithmically reduce the MRSA inoculum to zero colony forming units, while vancomycin required 24 h to achieve the same effect. Interestingly, the $2^{nd}$ generation phenylthiazole derivative 17 rapidly eliminated the bacterial cells within a 2 h window. These data confirm that the $2^{nd}$ generation phenylthiazoles maintained the selective advantage observed with the $1^{st}$ generation compounds over vancomycin and linezolid in terms of rate of elimination of MRSA cells.

Initial antibacterial screening for compounds 40-64 as compared with Vancomycin was conducted against one MRSA strain and the result is summarized in Table 7.

TABLE 7

The minimum inhibitory concentration (MIC in µg/mL) of compounds initially screened against methicillin-resistant *Staphylococcus aureus* (2658 RCMB).

| Compound | MRSA (2658 RCMB) |
|---|---|
| 40 | 6.25 |
| 41 | 25 |
| 42 | >50 |
| 43 | >50 |
| 47 | >50 |
| 48 | >50 |
| 49 | >50 |
| 50 | >50 |
| 51 | >50 |

TABLE 7-continued

The minimum inhibitory concentration (MIC in µg/mL) of compounds initially screened against methicillin-resistant *Staphylococcus aureus* (2658 RCMB).

| Compound | MRSA (2658 RCMB) |
|---|---|
| 52 | 25 |
| 53 | 6.25 |
| 54 | 1.17 |
| 55 | 1.56 |
| 56 | 1.56 |
| 57 | 1.56 |
| 58 | 1.17 |
| 59 | >50 |
| 60 | 50 |
| 61 | 1.17 |
| 62 | 3.12 |
| 63 | 0.78 |
| 64 | 0.78 |
| Vancomycin | 1.56 |

The five compounds identified from the initial screening with MIC values less than or equal to 1.2 µg/mL were selected for further evaluation (Table 8). In general, the tested compounds maintained their promising antibacterial activity against all tested methicillin-sensitive *S. aureus* (MSSA), MRSA and VRSA strains inhibiting growth at concentrations ranging from 2 to 8 µg/mL (except 64 which was inactive against *S. aureus* NRS107). This result correlates with the activity found for vancomycin (MIC ranges from 1-2 µg/mL against MRSA) and activity reported for cefatroline (G J Moran, *N. Engl. J. Med.* 2006, 355, 666-674) (MIC ranges from 0.5-4 µg/mL against MRSA and VRSA), a recently-approved antibacterial agent for treatment of MRSA infections. The MBC values for the compounds were equal to or one-fold higher than the compounds' MIC values against the tested strains which suggests that this series of phenylthiazoles are bactericidal agents.

TABLE 8

The minimum inhibitory concentration (MIC in µg/mL) and minimum bactericidal concentration (MBC in µg/mL) of tested compounds against methicillin-sensitive *Staphylococcus aureus*, methicillin-resistant *Staphylococcus aureus* (MRSA) and vancomycin-resistant *Staphylococcus aureus* (VRSA) strains.

| Bacterial Strains | | 54 | 58 | 61 | 63 | 64 | Vancomycin | Linezolid |
|---|---|---|---|---|---|---|---|---|
| S. aureus ATCC 6538 | MIC | 4 | 8 | 4 | 4 | 2 | 1 | 1 |
|  | MBC | 8 | 8 | 8 | 4 | 4 | 1 | 16 |
| S. aureus NRS107 | MIC | 4 | 8 | 8 | 4 | 64 | 2 | 1 |
|  | MBC | 8 | 8 | 8 | 4 | >64 | 2 | 16 |
| MRSA NRS119 | MIC | 8 | 8 | 8 | 4 | 4 | 1 | 32 |
|  | MBC | 8 | 8 | 8 | 4 | 4 | 1 | >64 |
| MRSA NRS123 (USA400) | MIC | 8 | 8 | 8 | 4 | 2 | 1 | 1 |
|  | MBC | 8 | 8 | 8 | 4 | 2 | 1 | 32 |
| MRSA NRS384 (USA300) | MIC | 8 | 8 | 4 | 4 | 4 | 1 | 1 |
|  | MBC | 8 | 8 | 8 | 4 | 4 | 1 | 32 |
| MRSA NRS385 | MIC | 8 | 8 | 4 | 4 | 4 | 1 | 2 |
|  | MBC | 8 | 8 | 8 | 4 | 4 | 1 | 16 |
| MRSA NRS386 | MIC | 8 | 8 | 8 | 4 | 2 | 1 | 2 |
|  | MBC | 8 | 8 | 8 | 4 | 2 | 1 | 64 |
| VRS10 (VRSA) | MIC | 8 | 8 | 8 | 4 | 2 | >64 | 1 |
|  | MBC | 8 | 8 | 8 | 4 | 4 | >64 | 64 |
| VRS12 (VRSA) | MIC | 8 | 8 | 8 | 4 | 4 | >64 | 1 |
|  | MBC | 8 | 8 | 8 | 4 | 4 | >64 | 64 |

We next moved to examine the antibacterial spectrum of this new series of phenylthiazoles against other clinically-relevant Gram-positive bacterial pathogens. Therefore, compounds 54, 58, 61, 63 and 64 were tested against *S. epidermidis*, *Enterococcus faecalis*, *E. faecium*, *Listeria monocytogenes*, and *Streptococcus pneumoniae* isolates (Table 9).

TABLE 9

The minimum inhibitory concentration (MIC in µg/mL) and minimum bactericidal concentration (MBC in µg/mL) of phenylthiazoles against Gram-positive bacterial pathogens including *S. epidermidis*, *E. faecalis*, *E. faecium*, *L. monocytogenes*, and *S. pneumoniae*.

| Compd/ Antibiotic | Methicillin-resistant Staphylococcus epidermidis NRS101 | | Enterococcus faecalis ATCC 51299 (VRE) | | Enterococcus faecium ATCC 700221 (VRE) | | Listeria monocytogenes ATCC 19111 | | Cephalosporin-resistant Streptococcus pneumoniae ATCC 51916 | | Methicillin-resistant Streptococcus pneumoniae ATCC 700677 | |
|---|---|---|---|---|---|---|---|---|---|---|---|---|
|  | MIC | MBC | MIC | MBC | MIC | MBC | MIC | MBC | MIC | MBC | MIC | MBC |
| 54 | 8 | 8 | 16 | 16 | 8 | 8 | 8 | 8 | 8 | 16 | 2 | 16 |
| 58 | 8 | 8 | 8 | 16 | 8 | 16 | 8 | 8 | 16 | 16 | 16 | 16 |
| 61 | 4 | 4 | 4 | 8 | 4 | 8 | 8 | 8 | 8 | 8 | 8 | 8 |
| 63 | 64 | >64 | 8 | 16 | 8 | 16 | 4 | 64 | 4 | 8 | 4 | 8 |
| 64 | 64 | >64 | 64 | >64 | 4 | 32 | 2 | 32 | 4 | 4 | 8 | 8 |
| Vancomycin | 1 | 1 | 16 | 64 | >64 | >64 | 1 | 1 | 2 | 2 | 2 | 2 |

Out of all pathogenic strains listed in Table 9, vancomycin-resistant enterococcal strains are a significant concern as they are leading sources of nosocomial infections. Interestingly, the nitrogenous side chains connected to the pyrimidine position-2 seem to have high impact on the anti-enterococcal activity of the compounds. The ethylenediamine, dimethylguanidine, morpholine carboxamidine and picolinimidamide (compounds 54, 58, 61 and 63) derivatives were found to be effective against both vancomycin-resistant *E. faecalis* and *E. faecium*. On the other hand, repositioning the nitrogen atom in the pyridine ring from position-3 to position-2 abolished the antibacterial activity observed against *E. faecalis* (Table 9).

The MBC values for most of the compounds were found to be equal to or one-fold higher than the compounds' MIC values against the tested bacterial strains indicating the compounds are bactericidal. The MBC values for 63 and 64 against *L. monocytogenes* were found to be more than three-fold higher than the compounds' MIC values indicating these compounds might be bacteriostatic against this particular strain or species.

To confirm the rapid bactericidal kinetics of this series of phenylthiazoles against MRSA, the five most promising derivatives were further evaluated via a time-kill assay. Compounds 54, 58 and 61 exhibited rapid bactericidal activity in vitro, completely eradicating the high inoculum of MRSA within two to four hours. Vancomycin required 24 hours to exert its bactericidal activity by causing a three-$\log_{10}$ reduction in the initial inoculum of MRSA. Compound 64 exhibited rapid bactericidal activity in vitro, decreasing the bacterial count by three-$\log_{10}$ within six hours and completely eradicated the bacterial CFU within 24 hours. Interestingly, compound 63 exhibited bacteriostatic activity by decreasing the MRSA CFU by only 2.3-log over 24 hours. This result confirms that phenylthiazoles with t-butyl lipophilic tail maintained the previously reported[16] unique advantage (i.e. rapid bactericidal activity in vitro) over the existing drug of choice; i.e. vancomycin, used in the treatment of invasive Gram-positive infections.

To detect the ability of MRSA to develop resistance, MRSA USA400 was exposed to sub-lethal doses of the ethylenediamine-containing derivative 54, to try to generate drug-resistant mutants via a multi-step resistance selection experiment (over 14 daily passages). The MIC for compound 54 increased only one-fold after the ninth passage but remained stable thereafter. In contrast, MRSA developed resistance rapidly to the antibiotic rifampicin as the MIC of the antibiotic increased 29-fold after only one passage and continued to increase rapidly (>500,000-fold increase in MIC by the ninth passage). The result indicates MRSA was unable to develop rapid resistance to 54, similar to the first-generation phenylthiazole compounds.

Next, we moved to investigate the selectivity of our compounds towards bacterial cells by measuring their toxicity to human colorectal cells. With the exception of compounds 58 and 64 that were intolerable at 32 µg/mL, the other three derivatives 54, 63 and 64 were highly tolerable at this concentration, which represents an eight to 30-fold difference when compared with the MIC value required to inhibit MRSA growth (reported in Tables 7 and 8).

Surface bound biofilm formation and prosthetic joints are inextricable. With the consistent upward increase in prosthetic joint replacements and other medical devices, the problem of recalcitrance to antibiotic treatment increased mainly due to biofilm-related infections. Bacterial biofilms are estimated to be a major source of infection (i.e. around 65% of human bacterial infections), particularly on indwelling medical devices. Staphylococci (namely *S. aureus* and *S. epidermidis*) are significant sources of biofilm-related infections. The biofilm is a complex structure that provides a natural shield to bacterial cells to most conventional antibiotics as these drugs cannot effectively penetrate the biofilm mass at an effective concentration. Thus finding antibacterial agents capable of disrupting these bacterial biofilms is important.

We evaluated the ability of the new series of phenylthiazole analogues to effectively disrupt adherent biofilm formed by MRSA via the microtiter dish biofilm formation assay. As noted earlier, many conventional antibiotics are ineffective at disrupting bacterial biofilms. This was observed with vancomycin, a cornerstone therapeutic for treatment of invasive MRSA infections, which exhibited very limited success in reducing MRSA biofilm mass, even at a high concentration, as has been previously reported. Briefly, at 1×MIC, vancomycin only disrupted 3% of MRSA biofilm mass. Even at a concentration of 32×MIC, vancomycin only was capable of reducing the biofilm mass by 34% (data not published). The findings are congruent with the reported reduced susceptibility of staphylococcal infections encased in biofilm to vancomycin. Other front-line alternative antibiotics such as linezolid and daptomycin have also shown limited success in disrupting/eradicating MRSA biofilm.

TABLE 10

In vivo PK parameters of compound 54 in rats after a single IV bolus injection.

| | $t_{1/2}$* (h) | CL (L/hr) | AUC mg · hr/L | Vβ (L) | Vdss (L) |
|---|---|---|---|---|---|
| 54 | 9.03 | 1.26 | 3.98 | 16.36 | 3.39 |

*$t_{1/2}$: half-life;
CL: clearance;
Vβ: volume of distribution in $2^{nd}$ compartment (peripheral tissues);
Vdss: volume of distribution at the steady state The growing threat from multidrug-resistant bacterial pathogens highlights a critical need to expand our currently available arsenal of antibiotics. The recently discovered phenylthiazoles class of antibacterial agents exhibited a promising antibacterial effect against several highly resistant strains of *S. aureus*, including MRSA.

The high potency of $1^{st}$ developed phenylthiazoles was plagued by their short half-life that did not exceed 30 min (due to rapid elimination in human liver microsomes). The main aim in this article was to develop $2^{nd}$ generation analogues with enhanced PK profiles. Thus, the hydrolysable C=N bond was buried inside a more metabolically stable pyrimidine nucleus. Then, the SAR at the cationic part was fully examined utilizing various nitrogenous moieties at the pyrimidine-2 position. Among the tested nitrogenous moieties, hydrazide and N,N-dimethylguanidine-containing derivatives 17 and 11 were found to be more potent than vancomycin, the drug of choice for treatment of systemic MRSA infections. By tuning the lipophilic moiety, the cyclohexenyl group was found to be the most active conformationally restricted analogue for the n-butyl moiety. Hence, the MIC value of 29 was one fold less than vancomycin and four times better than the $2^{nd}$ generation lead compound 8. In addition to the longer $t_{1/2}$ and better than expected safety margin, the $2^{nd}$ generation phenylthiazoles exhibited a selective advantage over vancomycin in term of rapid eradication of MRSA cells.

Replacement of the n-butyl with a t-butyl moiety provided a new series of phenylthiazoles characterized by a longer biological half-life. In addition to their promising antibacterial effect against different staphylococcal and enterococcal bacterial isolates, five derivatives were superior to vancomycin in their ability to disrupt MRSA biofilm mass in a concentration-dependent manner. More importantly, the multi-step resistance selection study indicated MRSA is unlikely to form rapid resistance to the new series of phenylthiazoles.

Experimental

Chemistry in General.

All biologically tested compounds are with purity not less than 95%. $^1$H NMR spectra were run at 300 or 400 MHz and $^{13}$C spectra were determined at 75.46 or 100 MHz in dimethyl sulfoxide (DMSO-$d_6$) on a Varian Mercury VX-300 or VX-400 NMR spectrometer. Chemical shifts are given in parts per million (ppm) on the delta (δ) scale. Chemical shifts were calibrated relative to those of the solvents.[35] Flash chromatography was performed on 230-400 mesh silica. The progress of reactions was monitored with Merck silica gel IB2-F plates (0.25 mm thickness). The infrared spectra were recorded in potassium bromide disks on pye Unicam SP 3300 and Shimadzu FT IR 8101 PC infrared spectrophotometer. Mass spectra were recorded at 70 eV. High resolution mass spectra were obtained from a Finnigan MAT XL95. Melting points were determined using capillary tubes with a Stuart SMP30 apparatus and are uncorrected. HPLC analyses were performed on Agilent binary HPLC system (Model 1260) equipped with a multiple wavelength absorbance UV detector set for 254 nM, and using a 5 μM C-18 reverse phase column. All cross-coupling reactions were conducted under nitrogen atmosphere, unless otherwise specified. All yields reported refer to isolated yields. Compounds 3 and 21 are previously reported (Mohammad, H, et al., *J. Med. Chem.* 2014, 57, 1609-1615).

(E)-1-[2-(4-Butylphenyl)-4-methylthiazol-5-yl]-3-(dimethyl-amino)prop-2-en-1-one (4)

To compound 3 (3.1 g, 11.3 mmol), DMF-DMA (3 mL) was added and the reaction mixture was heated at 80° C. for 12 h. After cooling the temperature down, the formed solid was collected by filtration, washed with petroleum ether and 35yridine35zed from ethanol to yield the desired product as an orange solid (3.3 g, 89%) mp=105.4° C.

$^1$H NMR (DMSO-$d_6$) δ: 7.84 (d, J=8 Hz, 2H), 7.69 (d, J=12.3 Hz, 1H), 7.31 (d, J=8.1 Hz, 2H), 5.44 (d, J=12 Hz, 1H), 3.15 (s, 3H), 2.89 (s, 3H), 2.65 (s, 3H), 2.60 (t, J=6.8 Hz, 2H), 1.58 (p, J=4.5 Hz, 2H), 1.32 (m, 2H), 0.88 (t, J=7.2 Hz, 3H); EIMS (m/z) 328 (58%).

Potassium salt of 4-[2-(4-Butylphenyl)-4-methylthiazol-5-yl]pyrimidine-2-thiolate (5)

To a solution of potassium hydroxide (200 mg, 3.5 mmol) and thiourea (500 mg, 6.5 mmol) in ethanol (15 mL), enaminone 4 (1 g, 3 mmol) was added. The reaction mixture was heated to reflux for 8 h, and then cooled down in a refrigerator at 8° C. The formed crystals were filtered and washed with diethyl ether to yield the final product as yellow crystals (1.1 g, 96%). Mp>300° C. $^1$H NMR (DMSO-$d_6$) δ: 8.02 (d, J=5.1 Hz, 1H), 7.86 (d, J=7.8 Hz, 2H), 7.32 (d, J=8.1 Hz, 2H), 6.75 (d, J=5.4 Hz, 1H), 2.60 (s, 3H), 2.49 (t, J=5.1 Hz, 2H), 1.55 (m, 2H), 1.32 (m, 2H), 0.91 (t, J=7.2 Hz, 3H).

2-(4-Butylphenyl)-4-methyl-5-(2-(methylthio)pyrimidin-4-yl)thiazole (6)

Method A:

To a solution of enaminone 4 (100 mg, 0.3 mmol) in ethanol (10 mL), S-methylisothiourea hemisulfate salt (160 mg, 0.6 mmol) and anhydrous potassium carbonate (200 mg, 1.4 mmol) were added. The reaction mixture was heated at reflux for 6 h. After completion of reaction, as monitored by TLC, ethanol was evaporated under reduced pressure and the crude product was purified by flash silica column chromatography using EtOAc-petroleum ether (1:1) to afford white solid (70 mg, 64%). Mp=112.7° C.; EIMS (m/z) 355 (31), 308 (100).

Method B:

To a solution of compound 5 (750 mg, 2.1 mmol) and potassium hydroxide (250 mg, 4.2 mmol) in water (15 mL), dimethyl sulfate (0.5 ml, 4 mmol) was added dropwise with vigorous stirring. After 2 h, the formed solid was filtered and washed with water to yield yellowish white powder (63 mg, 89%); mp=112.7° C. $^1$H NMR (DMSO-$d_6$) δ: 8.63 (d, J=5.1 Hz, 1H), 7.75 (d, J=7.8 Hz, 2H), 7.44 (d, J=5.1 Hz, 1H), 7.31 (d, J=7.8 Hz, 2H), 2.75 (s, 3H), 2.64 (t, J=7.2 Hz, 2H), 2.55 (s, 3H), 1.58 (p, J=7.2 Hz, 2H), 1.32 (m, 2H), 0.90 (t, J=7.2 Hz, 3H); EIMS (m/z) 355 (31), 308 (100).

2-(4-Butylphenyl)-4-methyl-5-(2-(methylsulfonyl)pyrimidin-4-yl)thiazole (7)

To a solution of compound 6 (500 mg, 1.4 mmol) in dry DCM (5 mL), m-CPBA (514 mg, 1.7 mmol) in DCM (5 mL) was added portion-wise with continuous stirring. After the reaction mixture was kept at 23° C. for 16 h, additional DCM (10 mL) was added and the reaction mixture was washed with 25 mL of a 5% aqueous solution of sodium metabisulfite, and 25 mL of 5% aqueous sodium carbonate. The organic layer was separated, dried and concentrated under reduced pressure to give the desired product as yellow crystals (520 mg, 95%) mp=100.5° C. $^1$H NMR (DMSO-$d_6$) δ: 8.99 (d, J=5.4 Hz, 1H), 8.66 (d, J=5.4 Hz, 1H), 7.89 (d, J=7.8 Hz, 2H), 7.34 (d, J=7.8 Hz, 2H), 2.93 (s, 3H), 2.63 (t, J=7.6 Hz, 2H), 2.61 (s, 3H), 1.57 (p, J=7.6 Hz, 2H), 1.33 (m, 2H), 0.90 (t, J=7.6 Hz, 3H); EIMS (m/z) 387 (12), 308 (100).

Compounds 8-15

To a solution of enaminone 4 (100 mg, 0.3 mmol) in absolute ethanol (5 mL), suitable guanidine or carbimidine (1.2 mmol) and potassium carbonate anhydrous (200 mg, 1.4 mmol) were added. The reaction mixture was heated at reflux for 8 h, ethanol was evaporated under reduced pressure and the reaction was quenched with cold water (50 mL). The formed flocculated solid was filtered, washed with water and purified with either acid-base extraction using HCl (1M, 50 mL) or flash silica column chromatography using EtOAc-petroleum ether-methanol (4.5:4.5:1) to yield the desired products. Physical properties and spectral analysis of isolated products are listed below:

4-[2-(4-Butylphenyl)-4-methylthiazol-5-yl]pyrimidin-2-amine (8)

Yellowish-white solid (70 mg, 71%) mp=159° C. $^1$H NMR (DMSO-$d_6$) δ: 8.32 (d, J=5.1 Hz, 1H), 7.86 (d, J=8.1 Hz, 2H), 7.33 (d, J=8.1 Hz, 2H), 6.91 (d, J=5.1 Hz, 1H), 6.74 (brs, 2H), 2.69 (s, 3H), 2.61 (t, J=7.2 Hz, 2H), 1.57 (q, J=7.2 Hz, 2H), 1.32 (q, J=7.2 Hz, 2H), 0.9 (t, J=9.6 Hz, 3H); CIMS m/z (rel intensity) 325 (MH$^+$, 100); HRMS (EI), m/z 324.1421 M$^+$, calcd for $C_{18}H_{20}N_4S$ 324.1409; HPLC purity 95.69% (Methanol-$H_2O$, 4:1).

4-[2-(4-Butylphenyl)-4-methylthiazol-5-yl]-N-methylpyrimidin-2-amine (9)

White solid (60 mg, 56%) mp=227° C. (charring); $^1$H NMR (DMSO-d$_6$) δ: 8.35 (d, J=5.4 Hz, 1H), 7.86 (d, J=7.8 Hz, 2H), 7.50 (brs, 1H), 7.31 (d, J=8.1 Hz, 2H), 6.93 (d, J=5.4 Hz, 1H), 2.72 (s, 3H), 2.64 (t, J=7.5 Hz, 2H), 2.50 (s, 3H), 1.58 (p, J=7.2 Hz, 2H), 1.3 (m, 2H), 0.89 (t, J=7.2 HZ, 3H); CIMS m/z (rel intensity) 339 (MH$^+$, 100); HRMS (EI), m/z 338.1569 M$^+$, calcd for C$_{19}$H$_{22}$N$_4$S 338.1565; HPLC purity 97.08% (Methanol-H$_2$O, 4:1).

N-{4-[2-(4-Butylphenyl)-4-methylthiazol-5-yl]pyrimidin-2-yl}cyanamide (10)

White solid (60 g, 28%) mp=118° C.; IR (KBr) cm$^{-1}$: 3383 (NH), 3184, 2935, 2160; $^1$H NMR (DMSO-d$_6$) δ: 8.17 (d, J=5.4 Hz, 1H), 7.91 (d, J=7.8 Hz, 2H), 7.36 (d, J=5.4 Hz, 2H), 6.66 (d, J=4.8 Hz, 1H), 6.55 (brs, 1H), 2.70 (s, 3H), 2.57 (t, J=7.4 Hz, 2H), 1.57 (p, J=7.5 Hz, 2H), 1.31 (six, J=7.5 Hz, 2H), 0.90 (t, J=7.2 Hz, 3H); CIMS m/z (rel intensity) 350 (MH$^+$, 100); HRMS (EI), m/z 349.1375 M$^+$, calcd for C$_{19}$H$_{19}$N$_5$S 349.1361; HPLC purity 96.1% (Methanol-H$_2$O, 4:1).

3-{4-[2-(4-Butylphenyl)-4-methylthiazol-5-yl]pyrimidin-2-yl}-1,1-dimethylguanidine (11)

Yellowish white solid (55 mg, 46%) mp=153.7° C.; $^1$H NMR (DMSO-d$_6$) δ:8.31 (d, J=7.2 Hz, 1H), 7.85 (d, J=8.4 Hz 2H), 7.32 (d, J=8.1 HZ, 2H), 7.14 (brs, 1H), 6.84 (d, J=6.4 Hz, 1H), 6.70 (brs, 1H), 3.33 (s, 6H), 2.69 (s, 3H), 2.61 (t, 2H), 1.56 (m, 2H), 1.3 (m, 2H), 0.90 (t, J=7.6 Hz, 3H). CIMS m/z (rel intensity) 395 (MH$^+$, 100); HRMS (EI), m/z 394.1944 M$^+$, calcd for C$_{21}$H$_{26}$N$_6$S 394.1940; HPLC purity 95.9% (Methanol-H$_2$O, 4:1).

1-{4-[2-(4-Butylphenyl)-4-methylthiazol-5-yl]pyrimidin-2-yl}thiourea (12)

White solid (78 mg, 33%) mp=212° C. (charring); $^1$H NMR (DMSO-d$_6$) δ: 8.33 (d, J=6.8 Hz, 1H), 7.86 (d, J=9.1 Hz, 2H), 7.34 (d, J=9.1 Hz, 2H), 6.91 (d, J=6.8 Hz, 1H), 6.71 (brs, 3H), 2.76 (s, 3H), 2.68 (t, J=7.6 Hz, 2H), 1.55 (m, 2H), 1.32 (m, 2H), 0.90 (t, J=7.2 Hz, 3H); CIMS m/z (rel intensity) 384 (MH$^+$, 100); HRMS (EI), m/z 383.1228 M$^+$, calcd for C$_{19}$H$_{21}$N$_5$S$_2$ 383.1238; HPLC purity 95.01% (Methanol-H$_2$O, 4:1).

2-(4-Butylphenyl)-4-methyl-5-[2-(38yridine-3-yl)pyrimidin-4-yl]thiazole (13)

White solid (50 mg, 23%) mp=167° C.; $^1$H NMR (DMSO-d$_6$) δ: 9.68 (s, 1H), 9.37 (d, J=5.1 Hz, 1H), 9.01 (d, J=6.4 Hz, 1H), 7.91 (d, J=6.0 Hz, 1H), 7.89 (d, J=9 Hz, 2H), 7.80 (t, J=6.4 Hz, 1H), 7.31 (d, J=9 Hz, 2H), 7.22 (d, J=5.1 Hz, 1H), 2.83 (s, 3H), 2.60 (t, J=7.2 Hz, 2H), 1.53 (p, J=7.2 Hz, 2H), 1.26 (m, 2H), 0.91 (t, J=7.2 Hz, 3H); EIMS m/z (rel intensity) 386 (MH$^+$, 100); HRMS (EI), m/z 386.1560 M$^+$, calcd for C$_{23}$H$_{22}$N$_4$S 386.1565; HPLC purity 98.46% (Methanol-H$_2$O, 4:1).

2-(4-Butylphenyl)-5-[2-(1H-pyrazol-1-yl)pyrimidin-4-yl]-4-methylthiazole (14)

White solid (55 mg, 46%) mp=163.7° C. $^1$H NMR (DMSO-d$_6$) δ: 8.33 (d, J=5.8 Hz, 1H), 8.03 (d, J=4.8 Hz, 1H), 7.85 (m, 1H), 7.80 (d, J=8.4 Hz, 2H), 7.31 (d, J=8.4 Hz, 2H), 6.87 (d, J=5.1 Hz, 1H), 6.59 (t, J=4.8 Hz, 1H), 2.71 (s, 3H), 2.60 (t, 2H), 1.6 (m, 2H), 1.3 (m, 2H), 0.9 (t, J=6.8 Hz, 3H); EIMS m/z (rel intensity) 375 (M$^+$, 100), calcd for C$_{21}$H$_{21}$N$_5$S 375; HPLC purity 95.58% (Methanol-H$_2$O, 4:1).

2-(4-Butylphenyl)-4-methyl-5-(2-(pyrrolidin-1-yl)pyrimidin-4-yl)thiazole (15)

Yellowish white solid (0.032 g, 29%) mp=153.7° C.; $^1$H NMR (DMSO-d$_6$) δ: 8.40 (d, J=5.4 Hz, 1H), 7.87 (d, J=7.8 Hz, 2H), 7.32 (d, J=7.8 Hz, 2H), 6.88 (d, J=4.8 Hz, 1H), 3.51 (s, 4H), 2.74 (s, 3H), 2.64 (t, J=7.2 Hz, 2H), 1.93 (m, 4H), 1.59 (m, 2H), 1.34 (m, 2H), 0.912 (t, J=7.2 Hz, 3H); CIMS m/z (rel intensity) 379 (MH$^+$, 100); HRMS (EI), m/z 378.1885 M$^+$, calcd for C$_{22}$H$_{26}$N$_4$S 378.1878; HPLC purity 97.91% (Methanol-H$_2$O, 4:1).

5-([1,2,4]Triazolo[1,5-a]pyrimidin-5-yl)-2-(4-butylphenyl)-4-methylthiazole (16)

To a solution of enaminone 4 (200 mg, 6 mmol) in absolute ethanol (5 mL), 4H-1,2,4-triazol-3-amine (100 mg, 0.5 mmol), and anhydrous potassium carbonate (100 mg, 0.7 mmol) were added, the reaction mixture was heated to reflux for 5 h, ethanol was evaporated under reduced pressure and the reaction was quenched with cold water (50 mL). The formed flocculated solid was filtered, washed with water and purified with flash silica column chromatography using EtOAc-hexane (1:1) to yield the desired product as a yellowish white solid (55 mg, 52%) mp=143° C.; $^1$H NMR (DMSO-d$_6$) δ: 8.95 (d, J=4.8 Hz, 1H), 8.78 (s, 1H), 7.85 (d, J=7.8 Hz, 2H), 7.68 (d, J=4.8 Hz, 1H), 7.24 (d, J=7.8 Hz, 2H), 2.75 (s, 3H), 2.62 (m, 2H), 1.58 (m, 2H), 1.27 (m, 2H), 0.92 (t, J=7.2 Hz, 3H); CIMS m/z (rel intensity) 350 (MH$^+$, 100); HRMS (EI), m/z 349.1375 M$^+$, calcd for C$_{19}$H$_{19}$N$_5$S 349.1361; HPLC purity 97.17% (Methanol-H$_2$O, 4:1).

2-(4-Butylphenyl)-5-(2-hydrazinopyrimidin-4-yl)-4-methylthiazole (17)

To a solution of methylsulfonylpyrimidine 7 (100 mg, 0.26 mmol) in DMF (2 mL), hydrazine hydrate (5 mL) was added. The reaction mixture was heated at 80° C. for 0.5 h. The formed fluffy solid was filtered and washed with boiled water to remove the residual hydrazine to finally give the titled product as a yellowish white fluffy powder (70 mg, 80%) mp=128° C.; $^1$H NMR (DMSO-d$_6$) δ: 8.38 (d, J=5.1 Hz, 1H), 8.28 (brs, 1H), 7.87 (d, J=8.1 Hz, 2H), 7.33 (d, J=7.8 Hz, 2H), 6.91 (d, J=6.8 HZ, 1H), 4.22 (brs, 2H), 2.72 (s, 3H), 2.63 (t, J=7.5 Hz, 2H), 1.58 (m, 2H), 1.32 (m, 2H), 0.90 (t, J=7.2 Hz, 3H); CIMS m/z (rel intensity) 340 (MH$^+$, 100); HRMS (EI), m/z 339.1526 M$^+$, calcd for C$_{18}$H$_{21}$N$_5$S 339.1518; HPLC purity 97.23% (Methanol-H$_2$O, 4:1).

2-(4-Butylphenyl)-5-(2-guanidinylpyrimidin-4-yl)-4-methylthiazole (18)

To a solution of methylsulfonylpyrimidine 7 (100 mg, 0.26 mmol) in dry DMF (5 mL), guanidine HCl (50 mg, 0.50 mmol) and potassium carbonate (100 mg, 0.7 mmol) were added. The reaction mixture was heated at 80° C. for 8 h, ethanol was evaporated under reduced pressure and cold water (10 mL) was added. The formed solid was filtered and crystallized from ethanol (95%) to yield the desired product as a yellowish brown solid (70 mg, 63%) mp=227.2° C.

(charring); ¹H NMR (DMSO-d$_6$) δ: 9.98 (brs, 1H), 8.56 (d, J=5.1 Hz, 1H), 8.01 (brs, 2H), 7.65 (d, J=10 Hz, 2H), 7.39 (d, J=8 Hz, 1H), 7.20 (brs, 2H), 7.05 (d, J=7.5 Hz, 2H), 2.50 (s, 3H), 2.43 (m, 2H), 1.42 (m, 2H), 1.19 (m, 2H), 0.77 (t, J=7.5 Hz, 3H); CIMS m/z (rel intensity) 367 (MH⁺, 100); HRMS (EI), m/z 366.1620 M⁺, calcd for C$_{19}$H$_{22}$N$_6$S 366.1627; HPLC purity 99.02% (Methanol-H$_2$O, 4:1).

2-{4-[42-(4-Butylphenyl)-4-methylthiazol-5-yl]pyrimidin-2-yl}-1,1,3,3-tetramethyl guanidine (19)

To a solution of methylsulfonylpyrimidine 7 (275 mg, 0.7 mmol) in dry DMF (5 mL), tetramethyl guanidine (0.5 mL) and potassium carbonate (100 mg, 0.7 mmol) were added. The reaction mixture was heated at 80° C. for 8 h, and then poured over an ice water (50 mL). The formed solid was filtered and purified by flash silica chromatography using system EtOAc-Hexan (9:1) to yield the desired product as yellow solid (21 mg, 7%). ¹H NMR (DMSO-d$_6$) δ: 8.65 (d, J=5.7 Hz, 1H), 7.90 (d, J=8.1 Hz, 2H), 7.59 (d, J=5.1 Hz, 1H), 7.34 (d, J=8.7 Hz, 2H), 2.70 (s, 12H), 2.63 (m, 2H), 2.57 (s, 3H), 1.57 (p, J=6.0 Hz, 2H), 1.32 (six., J=6.0 Hz, 2H), 0.90 (t, J=6.4 Hz, 3H); EIMS m/z (rel intensity) 422 (MH⁺, 31), 407 (100), calcd for C$_{23}$H$_{30}$N$_6$S 422; HPLC purity 95.06% (Methanol-H$_2$O, 4:1).

(E)-3-(Dimethylamino)-1-[2-(4-iodophenyl)-4-methylthiazol-5-yl]prop-2-en-1-one (22)

To a solution of compound 21 (1 g, 2.9 mml) in dry DMF (3 mL), DMF-DMA (0.5 mL, 4.5 mmol) was added and the reaction mixture was heated at 80° C. for 8 h. After cooling down, the reaction mixture was poured over crushed ice with vigorous stirring. The formed orange solid was collected by filtration and washed with water to yield the desired product as an orange solid (1.1 g, 95%) mp=157° C.; ¹H NMR (DMSO-d$_6$) δ: 7.86 (d, J=8.1 Hz, 2H), 7.72 (d, J=9.8 Hz, 2H), 7.71 (d, J=12.4 Hz, 1H), 5.42 (d, J=12.8 Hz, 1H), 3.10 (s, 3H), 2.89 (s, 3H), 2.66 (s, 3H); EIMS m/z (rel intensity) 398 (MH⁺, 60), calcd for C$_{15}$H$_{15}$IN$_2$OS 398.

4-[2-(4-Iodophenyl)-4-methylthiazol-5-yl]pyrimidin-2-amine (23)

To a solution of enaminone 22 (1.1 g, 2.7 mmol) in absolute ethanol (5 mL), guanidine hydrochloride (1 g, 10.5 mmol) and anhydrous potassium carbonate (1.5 g, 10.8 mmol) were added. The reaction mixture was heated at reflux for 12 h. After cooling, the white crystals that formed were filtered and washed with water to yield the desired product as a white solid (0.6 g, 66%) mp=114.3° C.; ¹H NMR (DMSO-d$_6$) δ: 8.33 (d, J=5.1 Hz, 1H), 7.88 (d, J=8.8 Hz, 2H), 7.73 (d, J=8.4 Hz, 2H), 6.91 (d, J=5.4 Hz, 1H), 6.91 (brs, 2H), 2.7 (s, 3H); CIMS m/z (rel intensity) 395 (MH⁺, 100); HRMS (EI), m/z 393.9756 M⁺, calcd for C$_{14}$H$_{11}$IN$_4$S 393.9749; HPLC purity 99.87% (Methanol-H$_2$O, 4:1).

4-[2-(4-Substituted)phenyl)-4-methylthiazol-5-yl]pyrimidin-2-amines (24-26)

To a solution of compound 23 (150 mg, 0.43 mmol) in dry DMF (5 mL), anhydrous potassium carbonate (250 mg, 1.7 mmol) and a catalytic amount of palladium X-Phos (Xphos Pd G2) (10 mg) were added. The reaction mixture was charged with an appropriate boronic acid derivative (1.2 equivalent). The mixture was irradiated in a SINEO microwave (Uwave-1000) for 1 h at 80° C., and then the reaction mixture was poured over crushed ice, filtered and washed with methanol to yield the desired product. The physical characteristics and spectral data of separated products are listed below.

4-{2-[4-(Furan-3-yl)phenyl]-4-methylthiazol-5-yl}pyrimidin-2-amine (24)

Yellow solid (100 mg, 78%) mp=161.2° C.; ¹H NMR (DMSO-d$_6$) δ: 8.33 (m, 1H), 8.31 (s, 1H), 7.97 (d, J=8.1 Hz, 2H), 7.75 (d, J=8.4 Hz, 2H), 7.04 (m, 1H), 6.92 (m, 2H), 6.73 (brs, 2H), 2.71 (s, 3H); CIMS m/z (rel intensity) 335 (MH⁺, 100); HRMS (EI), m/z 334.0892 M⁺, calcd for C$_{18}$H$_{14}$N$_4$OS 334.0888; HPLC purity 99.1% (Methanol-H$_2$O, 4:1).

4-{2-[4-(Furan-2-yl)phenyl]-4-methylthiazol-5-yl}pyrimidin-2-amine (25)

Brown solid (105 mg, 82%) mp=209.3° C.; ¹H NMR (DMSO-d$_6$) δ: 8.33 (d, J=6.1 Hz, 1H), 8.01 (d, J=8.6 Hz, 2H), 7.83 (m, 3H), 7.10 (d, J=3 Hz, 1H), 6.92 (d, J=4.8 Hz, 1H), 6.73 (brs, 2H), 6.65 (dd, J=4.5, 4.8 Hz, 1H), 2.70 (s, 3H); CIMS m/z (rel intensity) 335 (MH⁺, 100); HRMS (EI), m/z 334.0898 M⁺, calcd for C$_{18}$H$_{14}$N$_4$OS 334.0888; HPLC purity 98.75% (Methanol-H$_2$O, 4:1).

4-{4-Methyl-2-[4-(thiophen-3-yl)phenyl]thiazol-5-yl}pyrimidin-2-amine (26). Brown solid (120 mg, 90%) mp=225° C. (charring); ¹H NMR (DMSO-d$_6$) δ: 8.33 (d, J=5.1 HZ, 1H), 7.99 (m, 3H), 7.86 (d, J=8.4 Hz, 2H), 7.67 (d, J=2.7 Hz, 1H), 7.63 (d, J=3.9 Hz, 1H) 6.91 (d, J=5.1 Hz, 1H), 6.73 (brs, 2H), 2.71 (s, 3H); CIMS m/z (rel intensity) 351 (MH⁺, 100); HRMS (EI), m/z 350.0670 M⁺, calcd for C$_{18}$H$_{14}$N$_4$S$_2$ 350.0660; HPLC purity 98.97% (Methanol-H$_2$O, 4:1).

4-{2-[4-(Cycloalkenyl)phenyl]-4-methylthiazol-5-yl}pyrimidin-2-amines (27-35)

To a solution of compound 23 (150 mg, 0.43 mmol) in dry DMF (5 mL), triethylamine (0.2 mL, 1.9 mmol) and a catalytic amount of palladium acetate (20 mg) were added. Then, the flask was charged with an appropriate cycloalkene (2.4 mmol). The mixture was heated at 80° C. for 1 h, and then was filtered through celite 545, extracted with ethyl acetate and purified with flash silica column chromatography using eluent EtOAc-Hexane (1:9) to yield the desired product as presented below:

4-{2-[4-(Cyclopent-1-en-1-yl)phenyl]-4-methylthiazol-5-yl}pyrimidin-2-amine (27)

Off-white solid (50 mg, 39%) mp=160.6° C. ¹H NMR (DMSO-d$_6$) δ: 8.33 (d, J=5.4 Hz, 1H), 7.89 (d, J=7.8 Hz, 2H), 7.31 (d, J=7.8 Hz, 2H), 6.91 (d, J=5.4 Hz, 1H), 6.71 (brs., 2H), 5.81 (d, J=1.5 Hz, 1H), 2.70 (s, 3H), 1.69-1.48 (m, 2H), 1.23-1.54 (m, 2H), 0.85-0.78 (m, 2H); CIMS m/z (rel intensity) 335 (MH⁺, 100); HRMS (EI), m/z 334.1250 M⁺, calcd for C$_{19}$H$_{18}$N$_4$S 334.1252; HPLC purity 97.51% (Methanol-H$_2$O, 4:1).

4-{4-Methyl-2-[4-(4-methylcyclopent-1-en-1-yl)phenyl]thiazol-5-yl}pyrimidin-2-amine (28)

Off-white solid (60 mg, 45%) mp=141° C. ¹H NMR (DMSO-d$_6$) δ: 8.32 (d, J=5.1 Hz, 1H), 7.89 (d, J=7.8 Hz, 2H), 7.52 (d, J=7.8 Hz, 2H), 6.90 (d, J=5.1 Hz, 1H), 6.72

(brs., 2H), 5.84 (m, 1H), 2.70 (s, 3H), 1.28-1.69 (m, 4H), 0.92 (d, J=6.3 Hz, 3H), 0.85 (m, 1H); CIMS m/z (rel intensity) 349 (MH⁺, 100); HRMS (EI), m/z 348.1401 M⁺, calcd for C₂₀H₂₀N₄S 348.1409; HPLC purity 97.29% (Methanol-H₂O, 4:1).

4-{2-[4-(Cyclohex-1-en-1-yl)phenyl]-4-methylthiazol-5-yl}pyrimidin-2-amine (29)

Off-white solid (65 mg, 49%) mp=140.4° C. ¹H NMR (DMSO-d₆) δ: 8.32 (d, J=4.8 Hz, 1H), 7.89 (d, J=7.8 Hz, 2H), 7.39 (d, J=7.8 Hz, 2H), 6.91 (d, J=4.8 Hz, 1H), 6.80 (brs., 2H), 5.76 (d, J=1.5 Hz, 1H), 2.69 (s, 3H), 2.77-1.84 (m, 4H), 1.23-1.17 (m, 4H); CIMS m/z (rel intensity) 349 (MH⁺, 100); HRMS (EI), m/z 348.1414 M⁺, calcd for C₂₀H₂₀N₄S 348.1409; HPLC purity 96.64% (Methanol-H₂O, 4:1).

4-{2-[4-(Cyclohept-1-en-1-yl)phenyl]-4-methylthiazol-5-yl}pyrimidin-2-amine (30)

Off-white solid (100 mg, 73%) mp=164° C. ¹H NMR (DMSO-d₆) δ: 8.32 (d, J=4.8 Hz, 1H), 7.89 (d, J=7.8 Hz, 2H), 7.36 (d, J=7.8 Hz, 2H), 6.90 (d, J=4.8 Hz, 1H), 6.71 (brs, 2H), 5.86 (m, 1H), 2.69 (s, 3H), 2.69 (m, 2H), 2.263-2.15 (m, 2H), 1.85-1.71 (m, 2H), 1.49-1.38 (m, 2H), 1.22 (m, 2H); CIMS m/z (rel intensity) 363 (MH⁺, 100); HRMS (EI), m/z 362.1579 M⁺, calcd for C₂₁H₂₂N₄S 362.1565; HPLC purity 98.09% (Methanol-H₂O, 4:1).

4-{2-[4-(Cycloct-1-en-1-yl)phenyl]-4-methylthiazol-5-yl}pyrimidin-2-amine (31)

Off-white solid (120 mg, 84%) mp=188° C. ¹H NMR (DMSO-d₆) δ: 8.32 (d, J=5.1 Hz, 1H), 7.89 (d, J=7.8 Hz, 2H), 7.37 (d, J=7.8 Hz, 2H), 6.90 (d, J=5.1 Hz, 1H), 6.72 (brs., 2H), 5.71 (m, 1H), 2.69 (s, 3H), 2.28 (m, 2H), 1.75-1.48 (m, 10H); CIMS m/z (rel intensity) 377 (MH⁺, 100); HRMS (EI), m/z 376.1719 M⁺, calcd for C₂₂H₂₄N₄S 376.1722; HPLC purity 95.98% (Methanol-H₂O, 4:1).

4-{2-[4-(Cyclopentylidenemethyl)phenyl]-4-methylthiazol-5-yl}pyrimidin-2-amine (32)

Yellowish white solid (55 mg, 41%) mp=143° C.; ¹H NMR (DMSO-d₆) δ: 8.33 (d, J=5.4 Hz, 1H), 7.88 (d, J=8.4 Hz, 2H), 7.30 (d, J=8.4 Hz, 2H), 6.90 (d, J=5.4 Hz, 1H), 6.71 (brs, 2H), 5.38 (s, 1H), 2.70 (s, 3H), 2.27 (m, 1H), 2.16 (m, 1H), 1.82 (m, 2H), 1.22 (m, 4H); CIMS m/z (rel intensity) 349 (MH⁺, 100); HRMS (EI), m/z 348.1420 M⁺, calcd for C₂₀H₂₀N₄S 348.1409; HPLC purity 96.18% (Methanol-H₂O, 4:1).

4-{2-[4-(Cyclohexylidenemethyl)phenyl]-4-methylthiazol-5-yl}pyrimidin-2-amine (33)

Brown solid (60 mg, 44%) mp=165° C.; ¹H NMR (DMSO-d₆) δ: 8.33 (d, J=5.4 Hz, 1H), 7.91 (d, J=8.4 Hz, 2H), 7.33 (d, J=8.4 Hz, 2H), 6.91 (d, J=5.4 Hz, 1H), 6.72 (brs, 2H), 6.27 (s, 1H), 2.71 (s, 3H), 2.48 (m, 1H), 2.40 (m, 1H), 1.98-1.23 (m, 6H), 1.05 (m, 2H); CIMS m/z (rel intensity) 363 (MH⁺, 100); HRMS (EI), m/z 362.1570 M⁺, calcd for C₂₁H₂₂N₄S 362.1565; HPLC purity 99.72% (Methanol-H₂O, 4:1).

(E)-4-{2-[4-(2-Cyclopentylvinyl)phenyl]-4-methylthiazol-5-yl}pyrimidin-2-amine (34)

Brown solid (40 mg, 29%) mp=180.7° C.; ¹H NMR (DMSO-d₆) δ: 8.32 (d, J=5.4 Hz, 1H), 7.88 (d, J=8.1 Hz, 2H), 7.51 (d, J=8.1 Hz, 2H), 7.31 (dd, J=12, 6.8 Hz, 1H), 6.90 (d, J=5.4 Hz, 1H), 6.71 (brs, 2H), 6.44 (d, J=12.0 Hz, 1H), 2.69 (s, 3H), 2.21 (t, J=6 Hz, 1H), 1.95 (sep, J=7.5 Hz, 1H), 1.79-1.71 (m, 1H), 1.62-1.45 (m, 4H), 1.22-1.15 (m, 2H); CIMS m/z (rel intensity) 363 (MH⁺, 100); HRMS (EI), m/z 362.1559 M⁺, calcd for C₂₁H₂₂N₄S 362.1565; HPLC purity 95.33% (Methanol-H₂O, 4:1).

(E)-4-{2-[4-(2-Cyclohexylvinyl)phenyl]-4-methylthiazol-5-yl}pyrimidin-2-amine (35)

Brown solid (65 mg, 45%) mp=189° C. ¹H NMR (DMSO-d₆) δ: 8.32 (d, J=5.0 Hz, 1H), 7.95 (m, 1H), 7.88 (d, J=7.8 Hz, 2H), 7.51 (d, J=7.8 Hz, 2H), 6.90 (d, J=4.8 Hz, 1H), 6.80 (brs., 2H), 6.41 (m, 1H), 2.69 (s, 3H), 2.17 (m, 1H), 1.74 (m, 2H), 1.54-1.49 (m, 4H), 1.22-1.14 (m, 4H); CIMS m/z (rel intensity) 377 (MH⁺, 100); HRMS (EI), m/z 376.1731 M⁺, calcd for C₂₂H₂₄N₄S 376.1722; HPLC purity 95.03% (Methanol-H₂O, 4:1).

(E)-1-(2-(4-(tert-Butyl)phenyl)-4-methylthiazol-5-yl)-3-(dimethylamino)prop-2-en-1-one (39)

To compound 37 (3 g, 11 mmol), DMF-DMA (2.7 mL, 2.4 g, 20.4 mmol) was added and the reaction mixture was heated at 80° C. for 8 h. After cooling, the formed solid was collected by filtration, washed with petroleum ether and crystallized from ethanol to yield the desired product as an orange solid (3.4 g, 94.4%) mp=147° C.

¹H NMR (DMSO-d₆) δ: 7.86 (d, J=8.4 Hz, 2H), 7.71 (d, J=12.4 Hz, 1H), 7.51 (d, J=8.4 Hz, 2H), 5.44 (d, J=12.4 Hz, 1H), 3.14 (s, 3H), 2.87 (s, 3H), 2.64 (s, 3H), 1.29 (s, 9H); ¹³C NMR (DMSO-d₆) δ: 179.5, 166.1, 154.6, 154.5, 154.1, 134.2, 130.6, 126.5, 126.4, 94.2, 45.1, 37.7, 35.1, 31.3, 18.3; MS (m/z) 328. Anal. Calc. for: (C₁₉H₂₄N₂OS): C, 69.48; H, 7.36; N, 8.53%; Found: C, 69.46; H, 7.37; N, 8.55%.

Compounds 40-43. General Procedure

To a solution of enaminone 38 (0.2 g, 0.6 mmol) in absolute ethanol (5 mL), proper guanidine or carboximidate (1.25 mmol); namely: guanidine hydrochloride, N-methylguanidine hydrochloride, pyrrolidine-1-carboximidamide hydroiodide, nicotinimidamide hydrochloride, and anhydrous potassium carbonate (0.2 g, 1.4 mmol) were added. The reaction mixture was heated at reflux for 8 h, ethanol was evaporated under reduced pressure and the reaction was quenched with cold water (50 mL). The formed flocculated solid was filtered, washed with water and purified by crystallization from absolute ethanol or via acid-base extraction using HCl (1M, 50 mL). Upon neutralization with sodium carbonate to pH 7-8, the desired products were precipitated. The obtained solid was filtered, washed with a copious amount of distilled water and dried. Physical properties and spectral analysis of isolated products are listed below:

4-(2-(4-(tert-Butyl)phenyl)-4-methylthiazol-5-yl)pyrimidin-2-amine (40)

Following the general procedure (5.1.3), and using guanidine hydrochloride (0.115 g, 1.2 mmol), compound 40 was obtained as yellowish white solid (0.13 g, 71%) mp=230° C.

¹H NMR (DMSO-d₆) δ: 8.31 (d, J=5.2 Hz, 1H), 7.88 (d, J=8.4 Hz, 2H), 7.53 (d, J=8.4 Hz, 2H), 6.90 (d, J=5.2 Hz, 1H), 6.72 (brs, 2H), 2.68 (s, 3H), 1.29 (s, 9H); ¹³C NMR (DMSO-d₆) δ: 166.6, 163.8, 159.6, 158.3, 154.0, 153.2, 131.9, 130.6, 126.5, 126.4, 106.9, 35.1, 31.3, 18.6; MS (m/z)

324; HRMS (EI) m/z 324.1421 M+, calcd for $C_{18}H_{20}N_4S$ 324.1409; Anal. Calc. for: ($C_{18}H_{20}N_4S$): C, 66.64; H, 6.21; N, 17.27%; Found: C, 66.65; H, 6.22; N, 17.29%.

4-(2-(4-(tert-Butyl)phenyl)-4-methylthiazol-5-yl)-N-methylpyrimidin-2-amine (41)

Following the general procedure (5.1.3), and using N-methylguanidine hydrochloride (0.14 g, 1.2 mmol), compound 41 was obtained as white solid (0.18 g, 89%) mp=160° C.; $^1$H NMR (DMSO-$d_6$) δ: 8.33 (d, J=5.2 Hz, 1H), 7.88 (d, J=8.4 Hz, 2H), 7.52 (d, J=8.4 Hz, 2H), 7.18 (d, J=5.2 Hz, 1H), 6.87 (brs, 1H), 2.83 (s, 3H), 2.70 (s, 3H), 1.29 (s, 9H); $^{13}$C NMR (DMSO-$d_6$) δ: 166.6, 162.9, 159.4, 158.3, 154.0, 153.4, 131.8, 130.6, 126.5, 126.4, 106.6, 38.1, 31.3, 28.2, 18.6; MS (m/z) 338; HRMS (EI) m/z 338.1569 M+, calcd for $C_{19}H_{21}N_4S$ 338.1565; Anal. Calc. for: ($C_{19}H_{21}N_4S$): C, 67.42; H, 6.55; N, 16.55%; Found: C, 67.41; H, 6.56; N, 16.56%.

2-(4-((tert-Butyl)phenyl)-4-methyl-5-(2-(pyrrolidin-1-yl)pyrimidin-4-yl)thiazole (42)

Following the general procedure (5.1.3), and using pyrrolidine-1-carboximidamide hydroiodide (0.3 g, 1.2 mmol), compound 42 was obtained as brown solid (0.21 g, 93%) mp=203° C.; $^1$H NMR (DMSO-$d_6$) δ: 8.38 (d, J=5.2 Hz, 1H), 7.88 (d, J=8.4 Hz, 2H), 7.52 (d, J=8.4 Hz, 2H), 6.86 (d, J=5.2 Hz, 1H), 3.50 (m, 4H), 2.72 (s, 3H), 1.92 (m, 4H), 1.29 (s, 9H); $^{13}$C NMR (DMSO-$d_6$) δ: 166.5, 160.1, 159.2, 158.0, 154.0, 153.6, 131.6, 130.5, 126.5, 126.4, 106.1, 46.7, 35.1, 31.3, 25.3, 18.7; MS (m/z) 378; HRMS (EI) m/z 378.1883 M+, calcd for $C_{22}H_{26}N_4S$ 378.1878; Anal. Calc. for: ($C_{22}H_{26}N_4S$): C, 69.81; H, 6.92; N, 14.80%; Found: C, 69.80; H, 6.93; N, 14.82%.

2-(4-(tert-Butyl)phenyl)-4-methyl-5-(2-(pyridin-3-yl)pyrimidin-4-yl)thiazole (43)

Following the general procedure (5.1.3), and using nicotinimidamide hydrochloride (0.25 g, 1.6 mmol), compound 43 was obtained as light brown solid (0.14 g, 73.5%) mp=150° C.; $^1$H NMR (DMSO-$d_6$) δ: 9.53 (s, 1H), 8.95 (d, J=5.2 Hz, 1H), 8.74 (d, J=6.4 Hz, 1H), 8.66 (d, J=6.8 Hz, 1H), 7.94 (d, J=8.4 Hz, 2H), 7.75 (d, J=5.6 Hz, 1H), 7.60 (t, J=6.4 Hz, 1H), 7.53 (d, J=8.4 Hz, 2H), 2.81 (s, 3H), 1.30 (s, 9H); $^{13}$C NMR (DMSO-$d_6$) δ: 167.9, 162.1, 159.2, 158.2, 155.2, 154.3, 152.1, 149.4, 135.5, 132.7, 130.6, 130.3, 126.6, 126.5, 124.3, 116.7, 36.1, 31.3, 18.9; MS (m/z) 308; HRMS (EI) m/z 308.1340 M+, calcd for $C_{19}H_{20}N_2S$ 308.1347; Anal. Calc. for: ($C_{19}H_{20}N_2S$): C, 73.99; H, 6.54; N, 9.08%; Found: C, 73.98; H, 6.52; N, 9.09%.

2-(4-(tert-Butyl)phenyl)-4-methyl-5-(2-(methylthio)pyrimidin-4-yl)thiazole (45)

To a solution of potassium hydroxide (0.2 g, 3.5 mmol) and thiourea (0.5 g, 6.5 mmol) in ethanol (15 mL), enaminone 39 (1 g, 3 mmol) was added. The reaction mixture was heated to reflux for 8 h and then cooled down in an ice-bath to 8° C. The formed crystals were filtered and washed with diethyl ether to yield the potassium salt intermediate 44 as yellow solid (1.1 g, 96%) mp>300° C. $^1$H NMR (DMSO-$d_6$) δ:11.52 (brs, 1H), 8.64 (d, J=5.2 Hz, 1H), 7.91 (d, J=8.4 Hz, 2H), 7.51 (d, J=8.4 Hz, 2H), 7.37 (d, J=5.2 Hz, 1H), 2.75 (s, 3H) 1.30 (s, 9H); $^{13}$C NMR (DMSO-$d_6$) δ: 167.6, 159.4, 159.4, 158.0, 155.1, 154.3, 151.8, 130.3, 126.6, 126.5, 111.7, 35.1, 31.3, 18.7; MS (m/z) 341. To a solution of the obtained intermediate 44 (0.8 g, 2.1 mmol) and potassium hydroxide (0.25 g, 4.2 mmol) in water (15 mL), dimethyl sulfate (0.5 mL, 4 mmol) was added dropwise with vigorous stirring. After 2 h, the formed solid was filtered and washed with a copious amount of water to yield a yellowish white solid (0.67 g, 89%); mp=125° C. $^1$H NMR (DMSO-$d_6$) δ: 8.35 (d, J=4.8 Hz, 1H), 7.91 (d, J=8.4 Hz, 2H), 7.56 (d, J=8.4 Hz, 2H), 6.88 (d, J=4.8 Hz, 1H), 2.77 (s, 3H), 2.68 (s, 3H) 1.31 (s, 9H);
$^{13}$C NMR (DMSO-$d_6$) δ: 166.6, 162.9, 159.4, 158.1, 154.0, 153.4, 131.8, 130.5, 126.5, 126.4, 106.5, 35.1, 31.3, 28.2, 18.6; MS (m/z) 355. Anal. Calc. for: ($C_{19}H_{21}N_3S_2$): C, 64.19; H, 5.95; N, 11.82%; Found: C, 64.17; H, 5.97; N, 11.84%.

2-(4-(tert-Butyl)phenyl)-4-methyl-5-(2-(methylsulfonyl)pyrimidin-4-yl)thiazole (46)

To a solution of compound 45 (0.5 g, 1.4 mmol) in dry DCM (5 mL), m-CPBA (0.514 g, 2.9 mmol) in DCM (5 mL) was added portion-wise with continuous stirring. After the reaction mixture was kept at 23° C. for 16 h, additional DCM (10 mL) was added and the reaction mixture was washed with 25 mL of 5% aqueous solution of sodium metabisulfite and 25 mL of 5% aqueous sodium carbonate. The organic layer was separated, dried and concentrated under reduced pressure to give the desired product as yellow crystals (0.52 g, 95%) mp=190° C. $^1$H NMR (DMSO-$d_6$) δ: 8.93 (d, J=5.2 Hz, 1H), 7.87 (d, J=8.4 Hz, 2H), 7.82 (d, J=8.4 Hz, 2H), 7.48 (d, J=5.2 Hz, 1H), 3.47 (s, 3H), 2.76 (s, 3H), 1.29 (s, 9H); $^{13}$C NMR (DMSO-$d_6$) δ: 168.6, 165.3, 159.0, 158.3, 156.3, 154.7, 130.1, 130.0, 126.7, 126.6, 106.9, 50.3, 35.1, 31.2, 18.9; MS (m/z) 387; Anal. Calc. for: ($C_{19}H_{21}N_3O_2S_2$): C, 58.89; H, 5.46; N, 10.84%; Found: C, 58.87; H, 5.47; N, 10.86%.

Compounds 47-64. General Procedure

To a solution of 46 (0.1 g, 0.26 mmol) in dry DMF (5 mL), a proper amine, hydrazine, guanidine or caboximidate (0.4 mmol); namely: ethylamine, cyclopentylamine, cyclohexylamine, dimethylamine, azetidine hydrochloride, morpholine, azetidin-3-ol hydrochloride, ethylenediamine, hydrazine hydrate, guanidine hydrochloride, methylguanidine hydrochloride, 1,1-dimethylguanidine hydrochloride, N,N-tetramethyl guanidine, pyrrolidine-1-carboximidamide hydroiodide, morpholine-4-carboximidamide hydroiodide, 4-methylpiperazine-1-carboximidamide hydroiodide, picolinmidamide hydrochloride, nicotinimidamide hydrochloride, was added. The reaction mixture was heated at 80° C. for 0.5-8 h, and then poured over ice water (50 mL). The formed solid was filtered and washed with 50% ethanol and recrystallized from absolute ethanol. For 53, the crude solid was washed with boiling water to remove the residual hydrazine. Physical properties and spectral analysis of isolated products are listed below:

4-(2-(4-(tert-Butyl)phenyl)-4-methylthiazol-5-yl)-N-ethylpyrimidin-2-amine (47)

Following the general procedure above, and using ethylamine (18 μL, 0.4 mmol), compound 47 was obtained as yellow solid (0.06 g, 67%) mp=145.5° C.; $^1$H NMR (DMSO-$d_6$) δ: 8.33 (d, J=4.8 Hz, 1H), 7.88 (d, J=8.4 Hz, 2H), 7.53 (d, J=8.4 Hz, 2H), 7.24 (d, J=4.8 Hz, 1H), 6.86 (brs, 1H), 3.43 (q, J=4.8 Hz, 2H), 2.70 (s, 3H), 1.29 (s, 9H), 1.13 (t, J=4.8 Hz, 3H); $^{13}$C NMR (DMSO-d$_6$) δ: 166.6, 162.3, 159.4, 158.3, 154.0, 153.4, 131.8, 130.6, 126.5, 126.4, 106.6, 35.8, 35.1, 31.3, 18.6, 15.0; MS (m/z) 352; HRMS (EI) m/z 352.1721 M$^+$, calcd for C$_{20}$H$_{24}$N$_4$S 352.1722; Anal. Calc. for: (C$_{20}$H$_{24}$N$_4$S): C, 68.15; H, 6.86; N, 15.89%; Found: C, 68.14; H, 6.87; N, 15.88%.

4-(2-(4-(tert-Butyl)phenyl)-4-methylthiazol-5-yl)-N-cyclopentylpyrimidin-2-amine (48)

Following the general procedure above, and using cyclopentylamine (34 μL, 0.4 mmol), compound 48 was obtained as yellow solid (0.07 g, 74%) m.p.=168° C.; $^1$H NMR (DMSO-d$_6$) δ: 8.32 (d, J=4.8 Hz, 1H), 7.87 (d, J=8.4 Hz, 2H), 7.51 (d, J=8.4 Hz, 2H), 7.25 (brs, 1H), 6.84 (d, J=4.8 Hz, 1H), 4.21 (m, 1H), 2.70 (s, 3H), 1.93 (m, 2H), 1.69 (m, 2H), 1.53 (m, 4H), 1.29 (s, 9H); $^{13}$C NMR (DMSO-d$_6$) δ: 166.6, 162.2, 159.3, 158.3, 153.9, 153.3, 131.9, 130.6, 126.4, 126.4, 106.5, 52.7, 35.0, 32.6, 31.3, 23.9, 18.6; MS (m/z) 392; HRMS (EI) m/z 392.2028 M$^+$, calcd. for C$_{23}$H$_{28}$N$_4$S 392.2035; Anal. Calc. for: (C$_{23}$H$_{28}$N$_4$S): C, 70.37; H, 7.19; N, 14.27%; Found: C, 70.35; H, 7.18; N, 14.26%.

4-(2-(4-(tert-Butyl)phenyl)-4-methylthiazol-5-yl)-N-cyclohexylpyrimidin-2-amine (49)

Following the general procedure (5.1.6), and using cyclohexylamine (39 μL, 0.4 mmol), compound 49 was obtained as brown solid (0.06 g, 57%) mp=167° C.; $^1$H NMR (DMSO-d$_6$) δ: 8.33 (d, J=4.8 Hz, 1H), 7.89 (d, J=8.4 Hz, 2H), 7.54 (d, J=4.8 Hz, 2H), 7.11 (brs, 1H), 6.85 (d, J=4.8 Hz, 1H), 3.71 (m, 1H), 3.16 (m, 1H), 2.71 (s, 3H), 1.91 (m, 1H), 1.73 (m, 4H), 1.59 (m, 4H), 1.31 (s, 9H); $^{13}$C NMR (DMSO-d$_6$) δ: 166.6, 161.7, 159.6, 158.3, 154.0, 153.2, 131.8, 130.6, 126.5, 126.4, 106.5, 44.3, 35.1, 32.7, 31.3, 25.8, 25.3, 18.5; MS (m/z) 406; HRMS (EI) m/z 406.2202 M$^+$, calcd for C$_{24}$H$_{30}$N$_4$S 406.2191; Anal. Calc. for: (C$_{24}$H$_{30}$N$_4$S): C, 70.90; H, 7.44; N, 13.78%; Found: C, 70.91; H, 7.45; N, 13.77%.

4-(2-(4-(tert-Butyl)phenyl)-4-methylthiazol-5-yl)-N,N-dimethylpyrimidin-2-amine (50)

Following the general procedure (5.1.6), and using dimethylamine (18 μL, 0.4 mmol), compound 50 was obtained as yellow solid (0.08 g, 82%) mp=162° C.; $^1$H NMR (DMSO-d$_6$) δ: 8.40 (d, J=4.8 Hz, 1H), 7.88 (d, J=8.4 Hz, 2H), 7.52 (d, J=8.4 Hz, 2H), 6.87 (d, J=4.8 Hz, 1H), 3.15 (s, 6H), 2.71 (s, 3H), 1.30 (s, 9H); $^{13}$C NMR (DMSO-d$_6$) δ: 166.7, 161.9, 159.2, 157.9, 154.0, 153.5, 131.8, 130.5, 126.4, 126.4, 105.9, 36.9, 35.1, 31.3, 18.7; MS (m/z) 352; HRMS (EI) m/z 352.1745 M$^+$, calcd for C$_{20}$H$_{24}$N$_4$S 352.1722; Anal. Calc. for: (C$_{20}$H$_{24}$N$_4$S): C, 68.15; H, 6.86; N, 15.89%; Found: C, 68.16; H, 6.88; N, 15.90%.

5-(2-(Azetidin-1-yl)pyrimidin-4-yl)-2-(4-(tert-butyl)phenyl)-4-methylthiazole (51)

Following the general procedure (5.1.6), and using azetidine hydrochloride (0.04 g, 0.4 mmol), compound 51 was obtained as brown solid (0.06 g, 60%) mp=137° C.; $^1$H NMR (DMSO-d$_6$) δ: 8.37 (d, J=4.8 Hz, 1H), 7.88 (d, J=8.8 Hz, 2H), 7.51 (d, J=8.8 Hz, 2H), 6.93 (d, J=4.8 Hz, 1H), 4.07 (t, J=7.6 Hz, 4H), 2.7 (s, 3H), 2.28 (p, J=7.6 Hz, 2H), 1.29 (s, 9H); $^{13}$C NMR (DMSO-d$_6$) δ: 166.7, 162.8, 159.2, 158.1, 154.0, 153.8, 131.2, 130.5, 126.5, 126.4, 107.1, 50.3, 35.1, 31.3, 18.7, 16.2; MS (m/z) 364; HRMS (EI) m/z 364.1718 M$^+$, calcd for C$_{21}$H$_{24}$N$_4$S 364.1722; Anal. Calc. for: (C$_{21}$H$_{24}$N$_4$S): C, 69.20; H, 6.64; N, 15.37%; Found: C, 69.22; H, 6.65; N, 15.38%.

4-(4-(2-(4-(tert-Butyl)phenyl)-4-methylthiazol-5-yl)pyrimidin-2-yl) morpholine (52)

Following the general procedure (5.1.6), and using morpholine (35 μL, 0.4 mmol), compound 52 was obtained as orange solid (0.07 g, 70%) mp=122.8° C.;
$^1$H NMR (DMSO-d$_6$) δ: 8.42 (d, J=5.2 Hz, 1H), 7.86 (d, J=8.4 Hz, 2H), 7.49 (d, J=8.4 Hz, 2H), 6.92 (d, J=5.2 Hz, 1H), 3.70 (t, J=4.4 Hz, 4H), 3.67 (t, J=4.4 Hz, 4H), 2.69 (s, 3H), 1.27 (s, 9H); $^{13}$C NMR (DMSO-d$_6$) δ: 166.7, 161.9, 159.4, 158.1, 154.0, 153.6, 131.6, 130.5, 126.5, 126.4, 107.2, 66.4, 44.3, 35.1, 31.3, 18.7; MS (m/z) 394; HRMS (EI) m/z 394.1812 M$^+$, calcd for C$_{22}$H$_{26}$N$_4$OS 394.1827; Anal. Calc. for: (C$_{22}$H$_{26}$N$_4$OS): C, 66.98; H, 6.64; N, 14.20%; Found: C, 66.99; H, 6.65; N, 14.21%.

1-(4-(2-(4-(tert-Butyl)phenyl)-4-methylthiazol-5-yl)pyrimidin-2-yl)azetidin-3-ol (53)

Following the general procedure (5.1.6), and using azetidin-3-ol hydrochloride (0.04 g, 0.4 mmol), compound 53 was obtained as orange solid (0.06 g, 61%) mp=214° C.;
$^1$H NMR (DMSO-d$_6$) δ: 8.40 (d, J=4.8 Hz, 1H), 7.90 (d, J=8.4 Hz, 2H), 7.53 (d, J=8.4 Hz, 2H), 6.96 (d, J=4.8 Hz, 1H), 5.74 (brs, 1H), 4.59 (m, 1H), 4.29 (dd, J=4.4 Hz, J=4.8 Hz, 2H), 3.84 (dd, J=5.7 Hz, J=4.8 Hz, 2H), 2.72 (s, 3H), 1.31 (s, 9 h); $^{13}$C NMR (DMSO-d$_6$) δ: 166.8, 162.9, 159.3, 158.2, 154.1, 153.9, 131.2, 130.5, 126.5, 126.4, 107.2, 61.2, 60.3, 35.1, 31.3, 18.7; MS (m/z) 380; HRMS (EI) m/z 380.1675 M$^+$, calcd for C$_{21}$H$_{24}$N$_4$OS 380.1671; Anal. Calc. for: (C$_{21}$H$_{24}$N$_4$OS): C, 66.29; H, 6.36; N, 14.72%; Found: C, 66.28; H, 6.34; N, 14.70%.

N-(4-(2-(4-(tert-Butyl)phenyl)-4-methylthiazol-5-yl)pyrimidin-2-yl)ethane-1,2-diamine (54)

Following the general procedure (5.1.6), and using ethylenediamine (24 μL, 0.4 mmol), compound 54 was obtained as yellow solid (0.08 g, 85%) mp=145° C.; $^1$H NMR (DMSO-d$_6$) δ: 8.35 (d, J=5.2 Hz, 1H), 7.89 (d, J=8.4 Hz, 2H), 7.53 (d, J=8.4 Hz, 2H), 7.27 (brs, 1H), 6.89 (d, J=5.2 Hz, 1H), 3.17 (t, J=4.8 Hz, 2H), 2.85 (t, J=4.8 Hz, 2H), 2.71 (s, 3H), 1.82 (brs, 2H), 1.31 (s, 9H); $^{13}$C NMR (DMSO-d$_6$) δ: 166.7, 162.6, 159.4, 158.4, 154.0, 153.4, 131.8, 130.6, 126.5, 126.4, 106.8, 43.3, 40.5, 35.1, 31.3, 18.6; MS (m/z) 367; HRMS (EI) m/z 367.1830 M$^+$, calcd for C$_{20}$H$_{25}$N$_5$S 367.1831; Anal. Calc. for: (C$_{20}$H$_{25}$N$_5$S): C, 65.36; H, 6.86; N, 19.06%; Found: C, 65.35; H, 6.87; N, 19.07%.

2-(4-(tert-Butyl)phenyl)-5-(2-hydrazinylpyrimidin-4-yl)-4-methylthiazole (55)

Following the general procedure (5.1.6), and using hydrazine hydrate (5 mL), compound 55 was obtained as yellowish white fluffy powder (0.07 g, 80%) mp=151° C.;
$^1$H NMR (DMSO-d$_6$) δ: 8.38 (d, J=5.2 Hz, 1H), 8.29 (brs, 1H), 7.89 (d, J=8.8 Hz, 2H), 7.53 (d, J=8.8 Hz, 2H), 6.91 (d, J=5.2 Hz, 1H), 4.21 (brs, 2H), 2.73 (s, 3H), 1.29 (s, 9H); $^{13}$C NMR (DMSO-d$_6$) δ: 166.7, 164.6, 159.3, 158.1, 154.0, 153.7, 131.6, 130.5, 126.5, 126.4, 107.2, 35.1, 31.3, 18.7; MS (m/z) 339; HRMS (EI) m/z 339.1527 M$^+$, calcd for $C_{18}H_{21}N_5S$ 339.1518; Anal. Calc. for: ($C_{18}H_{21}N_5S$): C, 63.69; H, 6.24; N, 20.63%; Found: C, 63.67; H, 6.25; N, 20.64%.

1-(4-(2-(4-(tert-Butyl)phenyl)-4-methylthiazol-5-yl)pyrimidin-2-yl)guanidine (56)

Following the general procedure (5.1.6), and using guanidine hydrochloride (0.05 g, 0.5 mmol), compound 56 was obtained as yellowish solid (0.09 g, 95%) mp=275° C.; $^1$H NMR (DMSO-$d_6$) δ: 8.87 (brs, 1H), 8.44 (d, J=5.2 Hz, 1H), 8.41 (brs, 1H), 7.91 (d, J=8.2 Hz, 2H), 7.53 (d, J=8.2 Hz, 2H), 7.01 (d, J=5.2 Hz, 1H), 6.89 (brs, 2H), 2.75 (s, 3H), 1.30 (s, 9H); $^{13}$C NMR (DMSO-$d_6$) δ: 166.7, 159.8, 159.2, 158.3, 157.8, 154.0, 153.3, 131.9, 130.6, 126.5, 126.4, 106.0, 35.1, 31.3, 18.7; MS (m/z) 366; HRMS (EI) m/z 366.1640 M$^+$, calcd for $C_{19}H_{22}N_6S$ 366.1627; Anal. Calc. for: ($C_{19}H_{22}N_6S$): C, 62.27; H, 6.05; N, 22.93%; Found: C, 62.28; H, 6.06; N, 22.92%.

1-(4-(2-(4-(tert-Butyl)phenyl)-4-methylthiazol-5-yl)pyrimidin-2-yl)-3-methylguanidine (57)

Following the general procedure (5.1.6), and using methylguanidine hydrochloride (0.06 g, 0.5 mmol), compound 57 was obtained as yellowish solid (0.07 g, 65%) mp=236° C.; $^1$H NMR (DMSO-$d_6$) δ: 8.78 (brs, 1H), 8.53 (d, J=5.2, 1H), 8.33 (brs, 1H), 7.90 (d, J=8.4 Hz, 2H), 7.54 (d, J=8.4 Hz, 2H), 7.15 (brs, 1H), 6.87 (d, J=5.2 Hz, 1H), 2.85 (s, 3H), 2.77 (s, 3H), 1.31 (s, 9H); $^{13}$C NMR (DMSO-$d_6$) δ: 168.1, 166.7, 162.4, 159.2, 158.1, 154.0, 153.5, 140.8, 130.5, 126.5, 126.4, 107.0, 36.9, 35.1, 31.3, 18.6; MS (m/z) 380; HRMS (EI) m/z 380.1790 M$^+$, calcd for $C_{20}H_{24}N_6S$ 380.1783; Anal. Calc. for: ($C_{20}H_{24}N_6S$): C, 63.13; H, 6.36; N, 22.09%; Found: C, 63.12; H, 6.35; N, 22.11%.

3-(4-(2-(4-(tert-Butyl)phenyl)-4-methylthiazol-5-yl)pyrimidin-2-yl)-1,1-dimethylguanidine (58)

Following the general procedure (5.1.6), and using 1,1-dimethylguanidine hydrochloride (0.06 g, 0.5 mmol), compound 58 was obtained as yellowish solid (0.1 g, 85%) mp=215° C.; $^1$H NMR (DMSO-$d_6$) δ: 8.46 (d, J=5.2 Hz, 1H), 8.22 (brs, 2H), 7.89 (d, J=8.4 Hz, 2H), 7.53 (d, J=8.4 Hz, 2H), 7.02 (d, J=5.2 Hz, 1H), 3.01 (s, 6H), 2.68 (s, 3H), 1.30 (s, 9H); $^{13}$C NMR (DMSO-$d_6$) δ: 166.5, 165.9, 158.6, 158.5, 157.4, 154.0, 152.8, 132.4, 130.6, 126.5, 126.4, 107.7, 37., 35.1, 31.3, 18.6; MS (m/z) 394; HRMS (EI) m/z 394.1944 M$^+$, calcd for $C_{21}H_{26}N_6S$ 394.1940; Anal. Calc. for: ($C_{21}H_{26}N_6S$): C, 64.37; H, 6.21; N, 17.27%; Found: C, 64.35; H, 6.22; N, 17.28%.

N-2-(4-(2-(4-(tert-Butyl)phenyl)-4-methylthiazol-5-yl)pyrimidin-2-yl)-1,1,3,3-tetramethylguanidine (59)

Following the general procedure (5.1.6), and using N,N-tetramethyl guanidine (50 μL, 0.4 mmol), compound 59 was obtained as yellowish solid (0.09 g, 85%) mp=115° C.; $^1$H NMR (DMSO-$d_6$) δ: 8.46 (d, J=5.2 Hz, 1H), 7.88 (d, J=8.4 Hz, 2H), 7.52 (d, J=8.4 Hz, 2H), 7.03 (d, J=5.2 Hz, 1H), 2.73 (s, 12H), 2.68 (s, 3H), 1.29 (s, 9H); $^{13}$C NMR (DMSO-$d_6$) δ: 167.1, 166.7, 162.8, 159.5, 158.1, 153.9, 152.9, 131.6, 130.6, 126.5, 126.4, 107.8, 50.1, 35.1, 31.3, 18.64; MS (m/z) 422; HRMS (EI) m/z 422.2255 M$^+$, calcd for $C_{23}H_{30}N_6S$ 422.2253; Anal. Calc. for: ($C_{23}H_{30}N_6S$): C, 65.37; H, 7.16; N, 19.89%; Found: C, 65.35; H, 7.15; N, 19.87%.

N-(4-(2-(4-(tert-Butyl)phenyl)-4-methylthiazol-5-yl)pyrimidin-2-yl) pyrrolidine-1-carboximidamide (60)

Following the general procedure (5.1.6), and using pyrrolidine-1-carboximidamide hydroiodide (0.1 g, 0.4 mmol), compound 60 was obtained as yellowish solid (0.1 g, 92%) mp=190° C.; $^1$H NMR (DMSO-$d_6$) δ: 8.47 (d, J=4.8 Hz, 1H), 8.02 (brs, 2H), 7.90 (d, J=8.4 Hz, 2H), 7.54 (d, J=4.8 Hz, 2H), 7.02 (d, J=4.8 Hz, 1H), 3.42 (m, 4H), 2.69 (s, 3H), 1.88 (m, 4H), 1.31 (s, 9H); $^{13}$C NMR (DMSO-$d_6$) δ: 166.5, 166.0, 158.6, 157.4, 156.6, 154.0, 152.8, 132.5, 130.6, 126.5, 126.4, 107.5, 46.6, 35.1, 31.3, 25.3, 18.5; MS (m/z) 420; HRMS (EI) m/z 420.2110 M$^+$, calcd for $C_{23}H_{28}N_6S$ 420.2096; Anal. Calc. for: ($C_{23}H_{28}N_6S$): C, 65.68; H, 6.71; N, 19.98%; Found: C, 65.67; H, 6.73; N, 19.97%.

N-(4-(2-(4-(tert-Butyl)phenyl)-4-methylthiazol-5-yl)pyrimidin-2-yl) morpholine-4-carboximidamide (61)

Following the general procedure (5.1.6), and using morpholine-4-carboximidamide hydroiodide (0.1 g, 0.4 mmol), compound 61 was obtained as yellow solid (0.1 g, 85%) mp=220° C.; $^1$H NMR (DMSO-$d_6$) δ: 8.50 (d, J=4.8 Hz, 1H), 8.39 (brs, 1H), 7.91 (brs, 1H), 7.88 (d, J=8.4 Hz, 2H), 7.52 (d, J=8.4 Hz, 2H), 7.07 (d, J=4.6 Hz, 1H), 3.63 (m, 4H), 3.59 (m, 4H), 2.69 (s, 3H), 1.29 (s, 9H); $^{13}$C NMR (DMSO-$d_6$) δ: 166.6, 166.0, 158.5, 157.8, 157.6, 154.0, 153.0, 132.3, 130.5, 126.5, 126.4, 108.2, 66.4, 44.7, 35.1, 31.3, 18.6; MS (m/z) 436; HRMS (EI) m/z 436.2053 M$^+$, calcd for $C_{25}H_{24}N_6OS$ 436.2045; Anal. Calc. for: ($C_{23}H_{28}N_6OS$): C, 63.28; H, 6.45; N, 19.25%; Found: C, 63.26; H, 6.46; N, 19.27%.

N-(4-(2-(4-(tert-Butyl)phenyl)-4-methylthiazol-5-yl)pyrimidin-2-yl)-4-methylpiperazine-1-carboximidamide (62)

Following the general procedure (5.1.6), and using 4-methylpiperazine-1-carboximidamide hydroiodide (0.11 g, 0.4 mmol), compound 62 was obtained as yellow solid (0.07 g, 60%) mp=165° C.; $^1$H NMR (DMSO-$d_6$) δ: 8.48 (d, J=5.2 Hz, 1H), 8.37 (brs, 1H), 7.94 (brs, 1H), 7.89 (d, J=8.4 Hz, 2H), 7.53 (d, J=8.4 Hz, 2H), 7.07 (d, J=5.2 Hz, 1H), 3.58 (m, 4H), 2.72 (s, 3H), 2.33 (m, 4H), 2.19 (s, 3H), 1.29 (s, 9H); $^{13}$C NMR (DMSO-$d_6$) δ: 168.7, 166.7, 162.9, 159.4, 158.3, 154.0, 153.1, 131.4, 130.6, 126.5, 126.5, 107.0, 54.8, 46.1, 36.3, 35.1, 31.3, 18.9; MS (m/z) 449; HRMS (EI) m/z 449.2368 M$^+$, calcd for $C_{24}H_{31}N_7S$ 449.2362; Anal. Calc. for: ($C_{24}H_{31}N_7S$): C, 64.11; H, 6.95; N, 21.81%; Found: C, 64.13; H, 6.97; N, 21.83.

N-(4-(2-(4-(tert-Butyl)phenyl)-4-methylthiazol-5-yl)pyrimidin-2-yl) nicotinimidamide (63)

Following the general procedure (5.1.6), and using picolinimidamide hydrochloride (0.06 g, 0.4 mmol), compound 63 was obtained as orange-yellowish solid (0.1 g, 92%) mp=150° C.; $^1$H NMR (DMSO-$d_6$) δ: 9.53 (brs, 1H), 8.77 (d, J=4.4 Hz, 1H), 8.71 (d, J=5.2 Hz, 1H), 8.47 (d, J=4.8 Hz, 1H), 8.22 (brs, 1H), 7.93 (t, J=7.2 Hz, 1H), 7.64 (d, J=8.4 Hz, 2H), 7.61 (t, J=6.8 Hz, 1H), 7.52 (d, J=8.4 Hz, 2H), 7.39 (d, J=4.8 Hz, 1H), 2.68 (s, 3H), 1.29 (s, 9H); $^{13}$C NMR (DMSO-$d_6$) δ: 167.2, 166.9, 162.8, 159.0, 158.4, 158.0, 154.2, 151.9, 151.6, 149.0, 138.0, 131.7, 130.5, 126.5, 126.4, 122.6, 111.4, 35.1, 31.3, 18.7; MS (m/z) 428; HRMS (EI) m/z 428.1788 M$^+$, calcd for $C_{24}H_{24}N_6S$ 428.1783; Anal. Calc. for: ($C_{24}H_{24}N_6S$): C, 67.26; H, 5.64; N, 19.61%; Found: C, 67.25; H, 5.65; N, 19.63%.

N-(4-(2-(4-(tert-Butyl)phenyl)-4-methylthiazol-5-yl) pyrimidin-2-yl) picolinimidamide (64)

Following the general procedure (5.1.6), and using nicotinimidamide hydrochloride (0.06 g, 0.4 mmol), compound 64 was obtained as orange-yellowish solid (0.08 g, 69%) mp=170° C.; $^1$H NMR (DMSO-$d_6$) δ: 9.25 (brs, 1H), 8.73 (m, 2H), 8.44 (d, J=6.8 Hz, 1H), 8.22 (brs, 1H), 7.89 (m, 2H), 7.52 (m, 4H), 7.37 (d, J=4.8 Hz, 1H), 2.73 (s, 3H), 1.29 (s, 9H); $^{13}$C NMR (DMSO-$d_6$) δ: 167.2, 166.6, 159.4, 158.9, 158.3, 154.1, 153.8, 152.0, 149.1, 135.7, 131.9, 131.6, 130.4, 126.5, 126.5, 123.7, 111.3, 35.1, 31.3, 18.7; MS (m/z) 428; HRMS (EI) m/z 428.1790 M$^+$, calcd for $C_{24}H_{24}N_6S$ 428.1783; Anal. Calc. for: ($C_{24}H_{24}N_6S$): C, 67.26; H, 5.64; N, 19.61%; Found: C, 67.28; H, 5.66; N, 19.62%.

Antimicrobial Testing

Determination of Minimum Inhibitory Concentration (MIC).

MRSA clinical isolates, and vancomycin-resistant *Staphylococcus aureus* (VRSA) strain were obtained through the Network of Antimicrobial Resistance in *Staphylococcus aureus* (NARSA) program. In addition, vancomycin-resistant *Enterococcus faecium* (VRE) strain was obtained from the ATCC. Bacteria were cultured in cation-adjusted Mueller Hinton broth in a 96-well plate. Compounds, using triplicate samples, were added to the plate and serially diluted. Plates were incubated at 37° C. for 20 hours prior to determining the MIC. Plates were visually inspected and the MIC was categorized as the concentration at which no visible growth of bacteria was observed. The average of triplicate MIC determinations is reported.

The minimum inhibitory concentration (MIC) of tested compounds and control antibiotics were determined using the broth microdilution method in accordance with the recommendations contained in the Clinical and Laboratory Standards Institute guidelines, against methicillin-sensitive (ATCC 6538 and NRS107), methicillin-resistant (MRSA), and vancomycin-resistant (VRSA) *Staphylococcus aureus*, *Staphylococcus epidermidis*, *Enterococcus faecalis*, *E. faecium*, *Listeria monocytogenes*, and *Streptococcus pneumoniae* clinical isolates. A bacterial solution equivalent to 0.5 McFarland standard was prepared and diluted in cation-adjusted Mueller-Hinton broth (CAMHB) to achieve a bacterial concentration of about 5×10$^5$ CFU/mL and seeded in 96-well plates. *Enterococcus faecium* was diluted in brain heart infusion broth. *Enterococcus faecalis, Streptococcus pneumonia* and *Listeria monocytogenes* were diluted in tryptone soya broth (TSB). Compounds and control drugs were added in the first row of 96-well plates and serially diluted (to achieve a concentration gradient ranging from 128 to 1 µg/mL). Plates were then incubated aerobically at 37° C. for at least 18 hours. The minimum bactericidal concentration (MBC) of the active compounds was tested by plating 5 µL from wells with no growth onto Tryptic soy agar (TSA) plates. Plates were incubated at 37° C. for at least 18 hours before recording the MBC.

Time-Kill Assay.

MRSA (USA300) cells, in the logarithmic growth phase, were diluted to 1.0×10$^6$ colony-forming units (CFU/mL) and exposed to concentrations equivalent to 3.0×MIC (in triplicate) of tested compounds, and vancomycin in Tryptic soy broth (TSB) (Becton, Dickinson and Company, Sparks, Md., USA). Aliquots (100 µL) were taken from each sample after 2, 4, 6, 8, 10, 12, and 24 hours, serially diluted in phosphate-buffered saline, and transferred to Trypticase soy agar (TSA) (Becton, Dickinson and Company, Sparks, Md., USA) plates. Plates were incubated at 37° C. for at least 16 hours before counting viable CFU/mL to determine the time required to reduce the bacterial cell count by 3-$\log_{10}$.

In Vitro Cytotoxicity Analysis.

Compound 17 was assayed at concentrations of 8, 16, 32, 64, 128, and 256 µg/mL against an immortal keratinocyte cell line (HaCaT) in order to determine the potential toxic effect against mammalian cells in vitro. Cells were cultured in Dulbeco's modified Eagle's medium (Sigma-Aldrich, St. Louis, Mo., USA) with 10% fetal bovine serum (USA Scientific, Inc.) at 37° C. with 5% $CO_2$. Controls received DMSO alone at a concentration equal to that in drug-treated cell samples. The cells were incubated with the compounds in a 96-well plate at 37° C. and 5.0% $CO_2$ for 2 h prior to addition of the assay reagent MTS 3-(4,5-dimethylthiazol-2-yl)-5-(3-carboxymethoxyphenyl)-2-(4-sulfophenyl)-2H-tetrazolium) (Promega, Madison, Wis., USA). Corrected absorbance readings (actual absorbance readings for each treatment subtracted from background absorbance) were taken using a kinetic ELISA microplate reader (Molecular Devices, Sunnyvale, Calif., USA). The quantity of viable cells after treatment with each compound is expressed as a percentage of the control, DMSO.

Resistance Study Against MRSA.

To determine if MRSA would be capable of forming resistance to the compounds quickly, a multi-step resistance selection experiment was conducted, as described previously. The broth microdilution assay was utilized to determine the MIC of the tested compounds and rifampicin exposed to MRSA USA400 (NRS123) for 14 passages over a period of two weeks. Resistance was classified as a greater than four-fold increase in the initial MIC, as reported elsewhere.

In Vitro Cytotoxicity Analysis of Tested Compounds Against Caco-2 Cells.

Tested compounds were assayed (at concentrations of 16, 32, and 64 µg/mL) against a human colorectal (Caco-2) cell to determine the potential toxic effect to mammalian cells in vitro. Briefly, cells were cultured in Dulbecco's Modified Eagle Medium (DMEM) supplemented with 20% fetal bovine serum (FBS), non-essential amino acids (1×), and penicillin-streptomycin at 37° C. with $CO_2$ (5%). Control cells received DMSO alone at a concentration equal to that in drug-treated cell samples. The cells were incubated with the compounds (in triplicate) in a 96-well plate at 37° C. with $CO_2$ (5%) for two hours. The assay reagent MTS 3-(4,5-dimethylthiazol-2-yl)-5-(3-carboxymethoxyphenyl)-2-(4-sulfophenyl)-2H-tetrazolium) (Promega, Madison, Wis., USA) was subsequently added and the plate was incubated for four hours. Absorbance readings (at $OD_{490}$) were taken using a kinetic microplate reader (Molecular Devices, Sunnyvale, Calif., USA). The quantity of viable cells after treatment with each compound was expressed as a percentage of the viability of DMSO-treated control cells (average of triplicate wells±standard deviation). The toxicity data was analyzed via a two-way ANOVA, with post hoc Sidak's multiple comparisons test (P<0.05), utilizing GraphPad Prism 6.0 (GraphPad Software, La Jolla, Calif.).

MRSA Biofilm Eradication Assessment.

The compounds and vancomycin were examined for their ability to eradicate pre-formed, mature staphylococcal biofilm using the microtiter dish biofilm formation as say,[36] following the procedure described in a previous report.[28] An overnight culture of MRSA USA300 (NRS384) was diluted 1:100 in culture medium (Tryptic soy broth+1% glucose)

and incubated at 37° C. for 24 hours to form strong adherent biofilm. The bacterial suspension was removed and compounds were added at concentrations ranging from 128 to 1 µg/mL in TSB. Compounds were incubated with the biofilm at 37° C. for 24 hours. In order to quantify the biofilm mass, the bacterial suspension was removed and wells were washed with phosphate-buffered saline to remove planktonic bacteria. An aliquot of 0.1% crystal violet was added to each well to stain biofilm mass. After 30 minutes, wells were washed with sterile water and dried. Wells were de-stained using 100% ethanol prior to quantifying biofilm mass using a spectrophotometer ($OD_{595}$). Data are presented as percent eradication of MRSA USA300 biofilm for each test agent relative to the negative (DMSO) control wells. Data were analyzed using two-way ANOVA with post-hoc Sidak's test for multiple comparisons (P<0.05).

Caco-2 Permeability Assay.

Caco-2 cells (Cyprotex Inc.) grown in tissue culture flasks were trypsinized, suspended in medium, and the suspensions were applied to wells of a Millipore 96 well Caco-2 plate. The cells were allowed to grow and differentiate for three weeks, feeding at two-day intervals. For Apical to Basolateral (A→B) permeability, the tested compound was added to the apical (A) side and the amount of permeation was determined on the basolateral (B) side; for Basolateral to Apical (B→A) permeability, tested compound was added to the B side and the amount of permeation was determined on the A side. The A-side buffer contained 100 µM Lucifer yellow dye, in Transport Buffer (1.98 g/L glucose in 10 mM HEPES, 1.0× Hank's Balanced Salt Solution) pH 6.5, and the B-side buffer contained Transport Buffer at pH 7.4. Caco-2 cells were incubated with these buffers for 2 h, and the receiver side buffer was removed for analysis by LC/MS/MS. To verify the Caco-2 cell monolayers were properly formed, aliquots of the cell buffers were analyzed by fluorescence to determine the transport of the impermeable dye Lucifer Yellow. Any deviations from control values are reported. Data are expressed as permeability (Papp)=(dQ/dt)/$C_0$A where dQ/dt is the rate of permeation, $C_0$ is the initial concentration of test agent, and A is the area of the monolayer. In bidirectional permeability studies, the efflux ratio ($R_E$) is also calculated:

$R_E$=(Papp(B→A))/(Papp(A→B))

An $R_E$>2 indicates a potential substrate for P-glycoprotein or other active efflux transporters.

In vivo Pharmacokinetics. Pharmacokinetic studies were performed in male naïve Sprague-Dawley (SD) rats (three animals) following Institutional Animal Care and Use Committee guidelines. An IV bolus of a 5 µM solution of compound 19 was directly administered via tail-vein injection. Blood samples were collected over a 12-hour period post dose into Vacutainer tubes containing EDTA-K2. Plasma was isolated, and the concentration of tested compounds in plasma was determined with LC/MS/MS after protein precipitation with acetonitrile. Two-compartmental pharmacokinetic analysis was performed on plasma concentration data in order to calculate pharmacokinetic parameters.

PBS Solubility Screen.

Serial dilutions of the tested compounds, reserpine, tamoxifen, and verapamil were prepared in phosphate buffered saline (PBS) at 100× the final concentration. The solutions were diluted 100-fold into PBS in a 96-well plate and mixed. The absorbance of the PBS-containing plate was measured prior to addition of the test agents to determine the background absorbance. After 2 h, the presence of precipitate was detected by turbidity (absorbance at 540 nm). An absorbance value of greater than (mean+3× standard deviation of the blank), after subtracting the pre-experiment background, is indicative of turbidity. The solubility limit is reported as the highest experimental concentration with no evidence of turbidity.

Human Microsomal Stability Analysis.

The tested compounds were incubated in duplicate with human liver microsomes at 37° C. The reaction contained microsomal protein in 100 mM potassium phosphate, 2 mM NADPH, 3 mM $MgCl_2$, pH 7.4. A control was run for each test agent omitting NADPH to detect NADPH-free degradation. At 0, 10, 20, 40, and 60 minutes, an aliquot was removed from each experimental and control reaction and mixed with an equal volume of ice-cold Stop Solution (methanol containing haloperidol, diclofenac, or other internal standard). Stopped reactions are incubated at least ten minutes at –20° C., and an additional volume of water was added. The samples were centrifuged to remove precipitated protein, and the supernatants were analyzed by LC/MS/MS to quantitate the remaining parent. Data are converted to % remaining by dividing by the time zero concentration value. Data are fit to a first-order decay model to determine half-life. Intrinsic clearance is calculated from the half-life and the protein concentrations: $CL_{int}$=ln(2)/($T_{1/2}$ [microsomal protein]).

Statistical Analysis.

All statistical analysis was conducted using Kaleida Graph, version 4.03 (Synergy software, Reading, Pa.). Statistical significance was determined using ANOVA and the Fisher's Least Significant Difference (LSD) test with α=0.05.

In Vivo Pharmacokinetics.

This assay has been conducted at a credited bioequivalence center (http://www.grc-me.com/pk_pd.html). Pharmacokinetic studies were performed in male naïve Sprague-Dawley (SD) rats, (three animals) following Institutional Animal Care and Use Committee guidelines. Oral dosing was administered by gavage in a vehicle containing 5% ethanol, 45% PEG 400, and 50% water. Blood samples were collected over a 24 h period post dose into Vacutainer tubes containing EDTA-K2. Plasma was isolated, and the concentration of compound 17 in plasma was determined with LC/MS/MS after protein precipitation with acetonitrile.

Non-compartmental pharmacokinetic analysis was performed on plasma concentration data to calculate pharmacokinetic parameters using Kinetica® 2000 (release 4.4.1).

Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

What is claimed is:

1. A compound having formula (I)

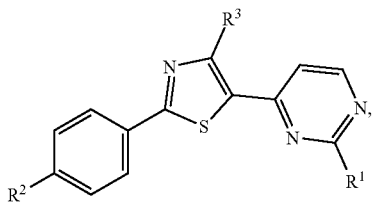

or a pharmaceutically acceptable salt, hydrate, or solvate thereof, wherein:
- $R^1$ is hydrogen, an alkylamino, hydrazines, guanidino, thioguanidino, cyano amino, ester, alkenyl, alkynyl, heteroalkenyl, heteroalkynyl, cycloalkyl, cycloalkenyl, cycloheteroalkyl, cycloheteroalkenyl, aryl, heteroaryl, arylalkyl, arylalkenyl, or arylalkynyl, each of which is optionally substituted; and
- $R^2$ is an azido, cyano, nitro, hydroxy, amino, thio, ester, amide, and derivatives thereof, and acyl, sulfoxyl, sulfonyl, phosphate, phosphoryl, alkenyl, alkynyl, heteroalkyl, heteroalkenyl, heteroalkynyl, heterocyclyl, cyclo alkyl, cycloalkenyl, cycloheteroalkyl, cycloheteroalkenyl, aryl, heteroaryl, arylalkyl, arylalkenyl, and arylalkynyl, each of which is optionally substituted; and
- $R^3$ is an alkenyl, alkynyl, heteroalkyl, heteroalkenyl, heteroalkynyl, heterocyclyl, cyclo alkyl, cycloalkenyl, cycloheteroalkyl, cycloheteroalkenyl, acyl, alkoxyl, aryl, heteroaryl, arylalkyl, arylalkenyl, or arylalkynyl, each of which is optionally substituted.

2. The compound of claim 1, wherein $R^1$ is an optionally substituted hydrazine.

3. The compound of claim 1, wherein $R^1$ is an alkylamino.

4. The compound of claim 1, wherein $R^1$ is an optionally substituted guanidino.

5. The compound of claim 4, wherein $R^1$ is guanidine or 3,3-dimethylguanidino.

6. The compound of claim 1, wherein $R^2$ is a cycloalkyl or cycloalkenyl.

7. The compound of claim 6, wherein $R^2$ is an optionally substituted cyclohexenyl.

8. The compound of claim 4, wherein $R^2$ is an optionally substituted cyclopentenyl.

9. The compound of claim 6, wherein $R^2$ is cyclohexylidenemethyl or cyclopentylidenemethyl.

10. The compound of claim 1, wherein $R^1$ is a thioguanidine.

11. A pharmaceutical composition comprising one or more compounds of claim 1, or a pharmaceutically acceptable salt thereof, together with one or more pharmaceutically acceptable carriers, diluents, and excipients.

12. A pharmaceutical composition comprising one or more compounds of claim 1, in combination with one or more other therapeutically active compounds by the same or different mode of action, and one or more pharmaceutically acceptable carriers, diluents, and excipients.

13. A method for treating a patient with microbial infections, the method comprising the step of administering a therapeutically effective amount of one or more compounds of claim 1 to the patient in need of relief from said infections.

14. A method for treating a patient with microbial infections, the method comprising the step of administering a therapeutically effective amount of one or more compounds of claim 1, together with one or more other therapeutically active compounds by the same or different mode of action, to the patient in need of relief from said infections.

15. A method for treating a patient with microbial infections, the method comprising the step of administering a therapeutically effective amount of one or more compounds of formula (I) to the patient in need of relief from said infections:

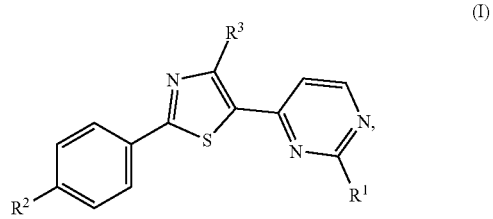

or a pharmaceutically acceptable salt, hydrate, or solvate thereof, wherein:
- $R^1$ is hydrogen, an alkylamino, hydrazines, guanidino, thioguanidino, cyano amino, ester, alkenyl, alkynyl, heteroalkenyl, heteroalkynyl, cycloalkyl, cycloalkenyl, cycloheteroalkyl, cycloheteroalkenyl, aryl, heteroaryl, arylalkyl, arylalkenyl, or arylalkynyl, each of which is optionally substituted; and
- $R^2$ is an azido, cyano, nitro, hydroxy, amino, thio, ester, amide, and derivatives thereof, and acyl, sulfoxyl, sulfonyl, phosphate, phosphoryl, alkenyl, alkynyl, heteroalkyl, heteroalkenyl, heteroalkynyl, heterocyclyl, cyclo alkyl, cycloalkenyl, cycloheteroalkyl, cycloheteroalkenyl, aryl, heteroaryl, arylalkyl, arylalkenyl, and arylalkynyl, each of which is optionally substituted; and
- $R^3$ is an alkenyl, alkynyl, heteroalkyl, heteroalkenyl, heteroalkynyl, heterocyclyl, cyclo alkyl, cycloalkenyl, cycloheteroalkyl, cycloheteroalkenyl, acyl, alkoxyl, aryl, heteroaryl, arylalkyl, arylalkenyl, or arylalkynyl, each of which is optionally substituted.

* * * * *